United States Patent
Kobayashi

(10) Patent No.: US 6,719,737 B2
(45) Date of Patent: Apr. 13, 2004

(54) SAFETY NEEDLE ASSEMBLY

(75) Inventor: Masahiko Kobayashi, Bear, DE (US)

(73) Assignee: Terumo Medical Corporation, Somerset, NJ (US)

( * ) Notice: Subject to any disclaimer, the term of this patent is extended or adjusted under 35 U.S.C. 154(b) by 0 days.

(21) Appl. No.: 10/143,092

(22) Filed: May 13, 2002

(65) Prior Publication Data
US 2003/0212369 A1 Nov. 13, 2003

(51) Int. Cl.[7] .................. A61M 5/00; A61M 5/32; B65D 83/10
(52) U.S. Cl. .................. 604/263; 604/192; 604/110; 604/199; 206/365
(58) Field of Search .................. 604/192–198, 604/263, 110, 162, 156, 117, 164.11, 403, 414, 200, 232, 500

(56) References Cited

U.S. PATENT DOCUMENTS

| | | |
|---|---|---|
| 3,658,061 A | 4/1972 | Hall |
| 4,747,836 A | 5/1988 | Luther |
| 4,820,277 A | 4/1989 | Norelli |
| 4,838,871 A | 6/1989 | Luther |
| 4,886,503 A | 12/1989 | Miller |
| 4,909,791 A | 3/1990 | Norelli |
| 4,909,792 A | 3/1990 | Norelli |
| 4,915,696 A | 4/1990 | Feimer |
| 4,944,731 A | 7/1990 | Cole |
| 4,950,249 A | 8/1990 | Jagger et al. |
| 4,982,842 A | 1/1991 | Hollister |
| 5,011,475 A | 4/1991 | Olson |
| 5,017,189 A | 5/1991 | Boumendil |
| 5,055,102 A | 10/1991 | Sitnik |
| 5,078,693 A | 1/1992 | Shine |
| 5,116,325 A | 5/1992 | Paterson |
| 5,135,509 A | 8/1992 | Olliffe |
| 5,139,489 A | 8/1992 | Hollister |
| 5,151,089 A | 9/1992 | Kirk, III et al. |
| 5,152,751 A | 10/1992 | Kozlowski |
| 5,154,285 A | 10/1992 | Hollister |
| 5,188,611 A | 2/1993 | Orgain |
| 5,207,653 A | 5/1993 | Janjua et al. |
| 5,232,454 A | 8/1993 | Hollister |
| 5,232,455 A | 8/1993 | Hollister |
| 5,242,417 A | 9/1993 | Paudler |
| 5,312,367 A | 5/1994 | Nathan |
| 5,312,369 A | 5/1994 | Arcusin et al. |
| 5,389,083 A | 2/1995 | McCarthy |

(List continued on next page.)

FOREIGN PATENT DOCUMENTS

| | | |
|---|---|---|
| JP | 2002-35128 A | 2/2002 |
| JP | 2002-102344 A | 4/2002 |

Primary Examiner—Brian L. Casler
Assistant Examiner—Roz Maiorino
(74) Attorney, Agent, or Firm—Burns, Doane, Swecker & Mathis, L.L.P.

(57) ABSTRACT

A safety needle assembly includes a hub having a proximal end for connection to a syringe and a distal end, a cannula provided with a lumen and having a proximal end connected to the distal end of the hub and a beveled distal end, and a collar formed separately from the hub and mounted on the hub in a rotationally fixed manner, with the collar including a sheath mounting portion. A removable protector is positioned over the cannula and covers the beveled distal end of the cannula. A sheath having an opening is pivotally connected to the sheath mounting portion of the collar and is positioned outside the protector when the protector is positioned over the cannula. The sheath is pivotally connected to the sheath mounting portion of the collar to be pivoted, after removal of the protector to expose the cannula, towards the cannula so that the cannula passes through the opening in the sheath and is covered by the sheath.

25 Claims, 24 Drawing Sheets

U.S. PATENT DOCUMENTS

| | | |
|---|---|---|
| 5,405,332 A | 4/1995 | Opalek |
| 5,445,619 A | 8/1995 | Burns |
| 5,486,163 A | 1/1996 | Haynes |
| 5,490,841 A | 2/1996 | Landis |
| 5,496,274 A * | 3/1996 | Graves et al. ............ 604/86 |
| 5,509,907 A | 4/1996 | Bevilacqua |
| 5,584,816 A * | 12/1996 | Gyure et al. ............ 604/192 |
| 5,599,313 A | 2/1997 | Gyure et al. |
| 5,599,318 A | 2/1997 | Sweeney et al. |
| 5,632,732 A * | 5/1997 | Szabo et al. ............ 604/192 |
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,672,161 A | 9/1997 | Allen et al. |
| 5,693,022 A | 12/1997 | Haynes |
| 5,704,920 A | 1/1998 | Gyure |
| 5,733,265 A | 3/1998 | Bachman et al. |
| 5,738,665 A | 4/1998 | Caizza et al. |
| 5,746,726 A | 5/1998 | Sweeney et al. |
| 5,807,351 A | 9/1998 | Kashmer |
| 5,836,920 A | 11/1998 | Robertson |
| 5,868,716 A | 2/1999 | Sweeney et al. |
| 5,891,103 A | 4/1999 | Burns |
| 5,910,130 A | 6/1999 | Caizza et al. |
| 5,913,846 A | 6/1999 | Szabo |
| 5,919,165 A | 7/1999 | Benson |
| 5,925,032 A | 7/1999 | Clements |
| 5,993,426 A | 11/1999 | Hollister |
| 6,186,325 B1 * | 2/2001 | Schmidt et al. ............ 206/364 |

* cited by examiner

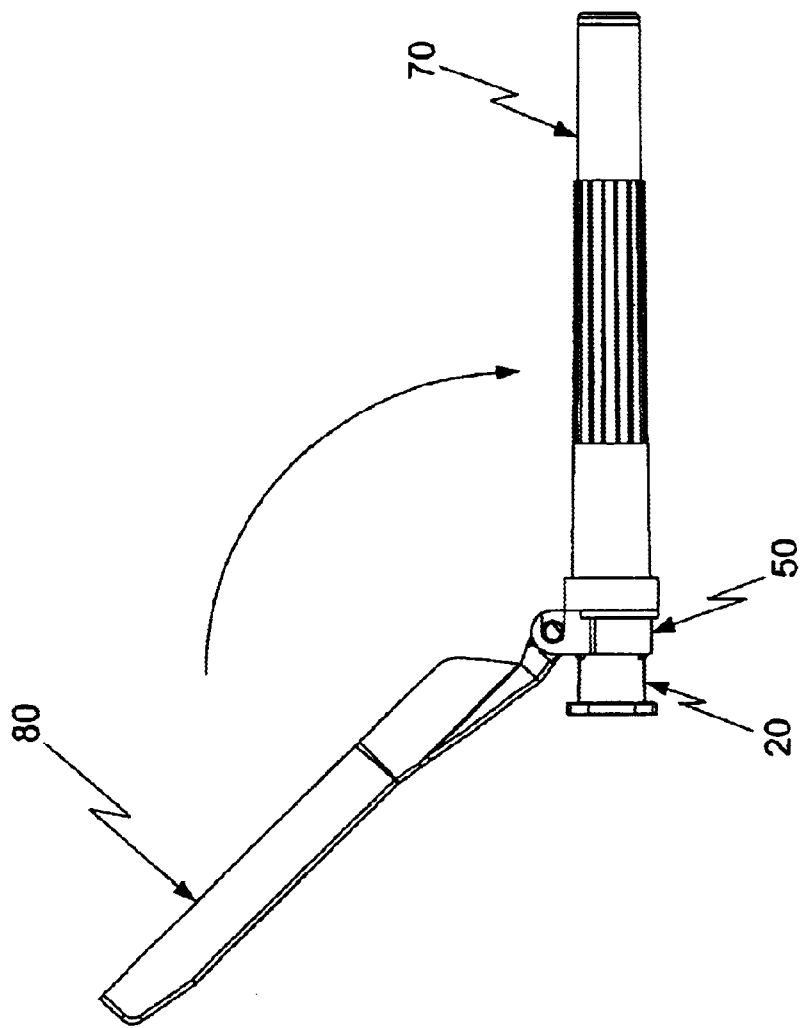

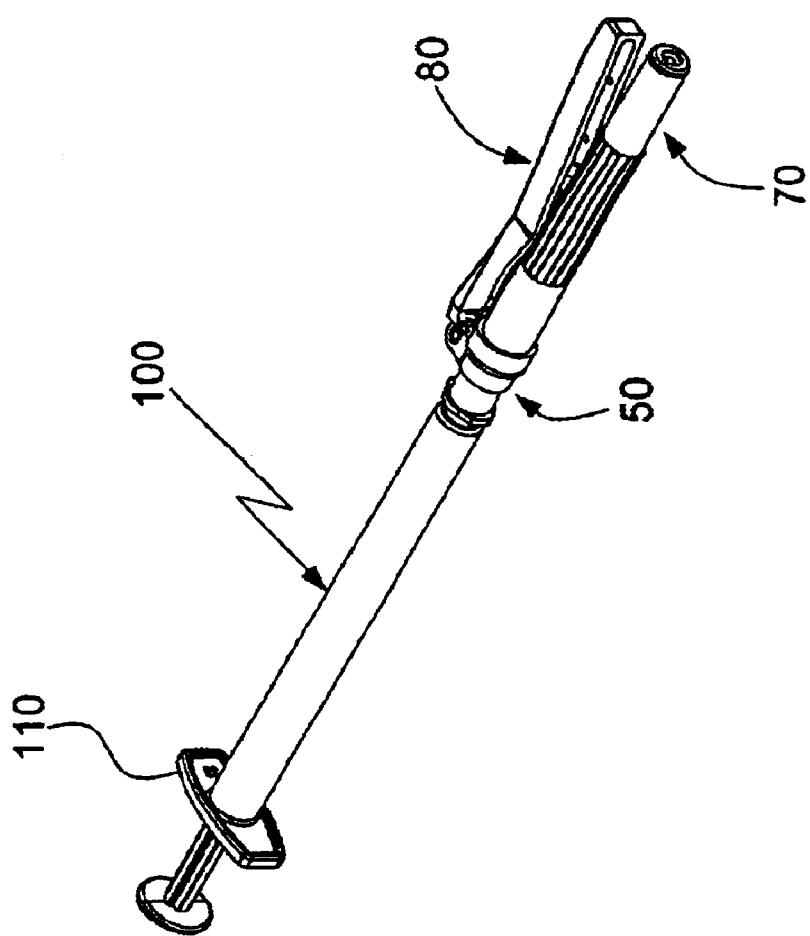

SAFETY NEEDLE ASSEMBLY

FIELD OF THE INVENTION

The present invention generally relates to needle assemblies. More particularly, the present invention pertains to a safety mechanism for use in connection with needle assemblies including hypodermic needles, catheter needles and other medical instruments.

BACKGROUND OF THE INVENTION

Needle assemblies used in medical procedures have been and continue to be a concern from the standpoint of healthcare worker safety. For example, accidental needlesticks with a used needle present the possibility for transmission of disease. A basic form of needlestick prevention involves the use of a rigid cylindrical cap which is positioned over the cannula and engages the hub to which the cannula is connected. During use, the cylindrical cap is removed to expose the cannula. After using the syringe/needle assembly for its intended procedure, the cylindrical cap must be once again mounted on the hub to cover the used cannula. Oftentimes, the healthcare professional tries to reposition the cylindrical cap on the syringe/needle assembly by "scooping" the cylindrical cap with the syringe/needle assembly. As can be appreciated, this may not be an easy or effective technique for repositioning the protective cap on the syringe/needle assembly. Also, the cap may become accidentally dislodged from the syringe/needle assembly, thus exposing the used cannula and presenting a potential danger.

Other proposals have also been made to protect healthcare professionals from needle stick hazards. These proposals are generally divided into three categories: 1) hinged recap devices in which a hinged sleeve is pivoted into a permanently locked position with respect to the cannula; 2) spring-loaded retractable cannula devices in which a spring-connected cannula is activated and the cannula in turn is retracted into the syringe barrel or the syringe plunger; and 3) sliding barrel devices in which the syringe barrel is formed by two concentric cylinders, the outer one of which is slid by the health care worker towards the cannula after use to cover the cannula. Although these assemblies provide some measure of protection against accidental needlesticks, difficulties remain.

For example, hinged recap devices are assembled between the syringe and needle assembly. This construction introduces dead space between the cannula and the syringe, thereby resulting in the waste of expensive medication. Retractable cannula devices run the risk of inadvertently retracting, thus wasting a syringe and once again presenting the possibility of wasting expensive medication. Additionally, the velocity of the cannula retraction could result in the spraying or splashing of fluids or medication, thus actually increasing the healthcare professional's exposure risk. The sliding barrel design is disadvantageous in that it almost doubles the length of the syringe from the unused position to the used/disabled/engaged position, thus substantially increasing the volume of biohazard waste and possibly creating exposure hazards because the syringe/needle assembly does not adequately fit into the sharps container.

Other concerns associated with at least the hinged recap devices relate to packaging and usage. When using hinges recap devices, it may be desirable to rotationally fix the position of the hinged sleeve relative to the cannula so that the hinge sleeve does not rotate relative to the cannula and hub during use. However, the distal end of the cannula is typically provided with a bevel which at least some users prefer to orient in a particular direction during use. If the hinged sleeve is designed to be rotationally fixed, the hinged sleeve may interfere with the user's view or manipulation of the cannula during use.

From the standpoint of packaging, it is preferable to be able to package the syringe and needle assembly with the attached hinged recap device in as small a package as possible. This helps reduce packaging costs while also reducing the amount of storage space required to store and/or transport the product. With hinged recap devices, particularly those in which the syringe and needle assembly are packaged with the hinged sleeve positioned to the side of the cannula, packaging costs can be of particular concern.

In light of at least the foregoing, a need exists for a safety needle assembly that is constructed to provide the desired protection against accidental needle sticks while also being constructed to facilitate usage by the user and to minimize packaging costs.

SUMMARY OF THE INVENTION

According to one aspect, a safety needle assembly includes a hub which includes a proximal end for connection to a syringe and a distal end, a cannula provided with a lumen and including a proximal end connected to the distal end of the hub and a beveled distal end, and a collar formed separately from the hub and mounted on the hub in rotationally fixed manner, with the collar including a sheath mounting portion. A protector is positioned over the cannula and covers the beveled distal end of the cannula, with the protector being removable to expose the cannula including the beveled distal end. A sheath includes an opening extending along at least a portion of the longitudinal extent of the sheath. The sheath is positioned outside the protector when the protector is positioned over the cannula and is pivotally connected to the sheath mounting portion of the collar to be pivoted, after removal of the protector to expose the cannula, towards the cannula so that the cannula passes through the opening in the sheath and is covered by the sheath.

Another aspect involves a safety needle assembly that includes a hub which includes a proximal end for connection to a syringe and a distal end, a cannula including a proximal end fixed to the distal end of the hub, with the cannula also including a lumen extending through the cannula and a distal end, a collar formed separately from the hub and mounted on the hub, with the collar including a pair of spaced apart mounting ears and with each of the mounting ears including two oppositely facing side surfaces. One of the side surfaces of one mounting ear faces one of the side surfaces of the other mounting ear, and each mounting ear has a width measured in a widthwise direction between distal and proximal ends of the mounting ear. One of the side surfaces of each mounting ear is provided with a first groove extending in the widthwise direction from a distal side of the mounting ear toward a proximal side of the mounting ear and the other side surface of each mounting ear is provided with a second groove extending in the widthwise direction from the proximal side of the mounting ear toward the distal side of the mounting ear, and each of the mounting ears is provided with a through hole formed by the overlapping first and second grooves. A protector is positioned over the cannula and covers the distal end of the cannula, with the protector being removable to expose the distal end of the cannula. A sheath is provided with an interior and an opening extending along at least a portion of a longitudinal extent of the sheath, with the sheath including a pair of pins each positioned in the through hole in one of the mounting ears to pivotally connect the sheath to the collar at a position outside the protector to permit the sheath, after removal of the protector to expose the distal end of the cannula, to pivot towards the cannula so that the cannula passes through the opening in the sheath and is positioned in the interior of the sheath in a position covered by the sheath.

BRIEF DESCRIPTION OF THE DRAWING FIGURES

The foregoing and additional features and characteristics of the present invention will become more apparent from the following detailed description considered with reference to the accompanying drawing figures in which like reference numerals designate like elements.

Figure 15:
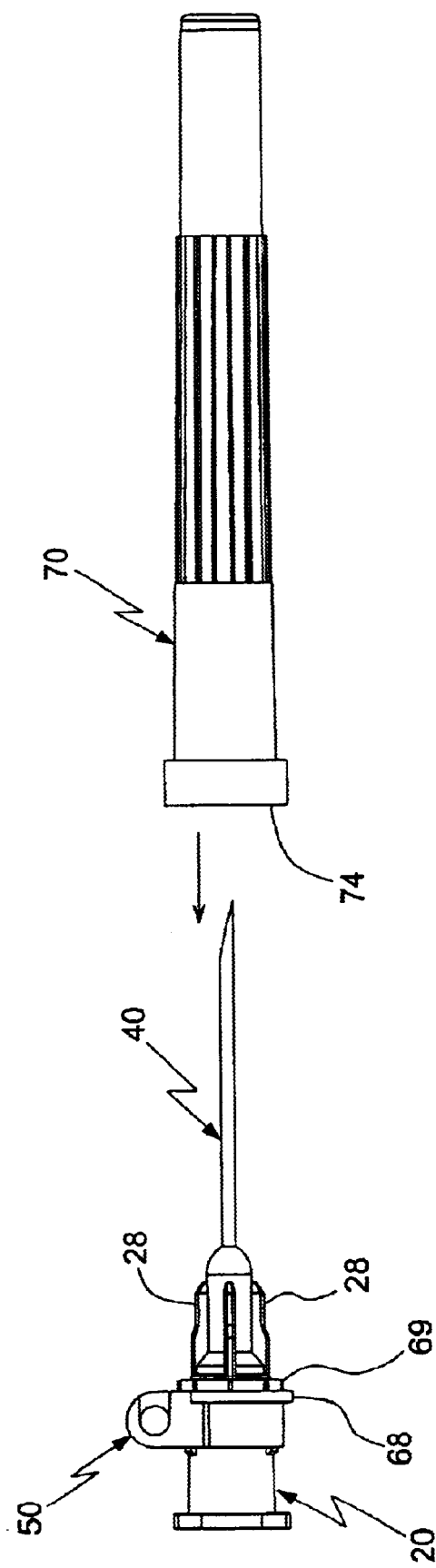

FIG. 15 generally illustrates another aspect of the assembly procedure in which the protector is being mounted in covering relation to the cannula.

Figure 16:
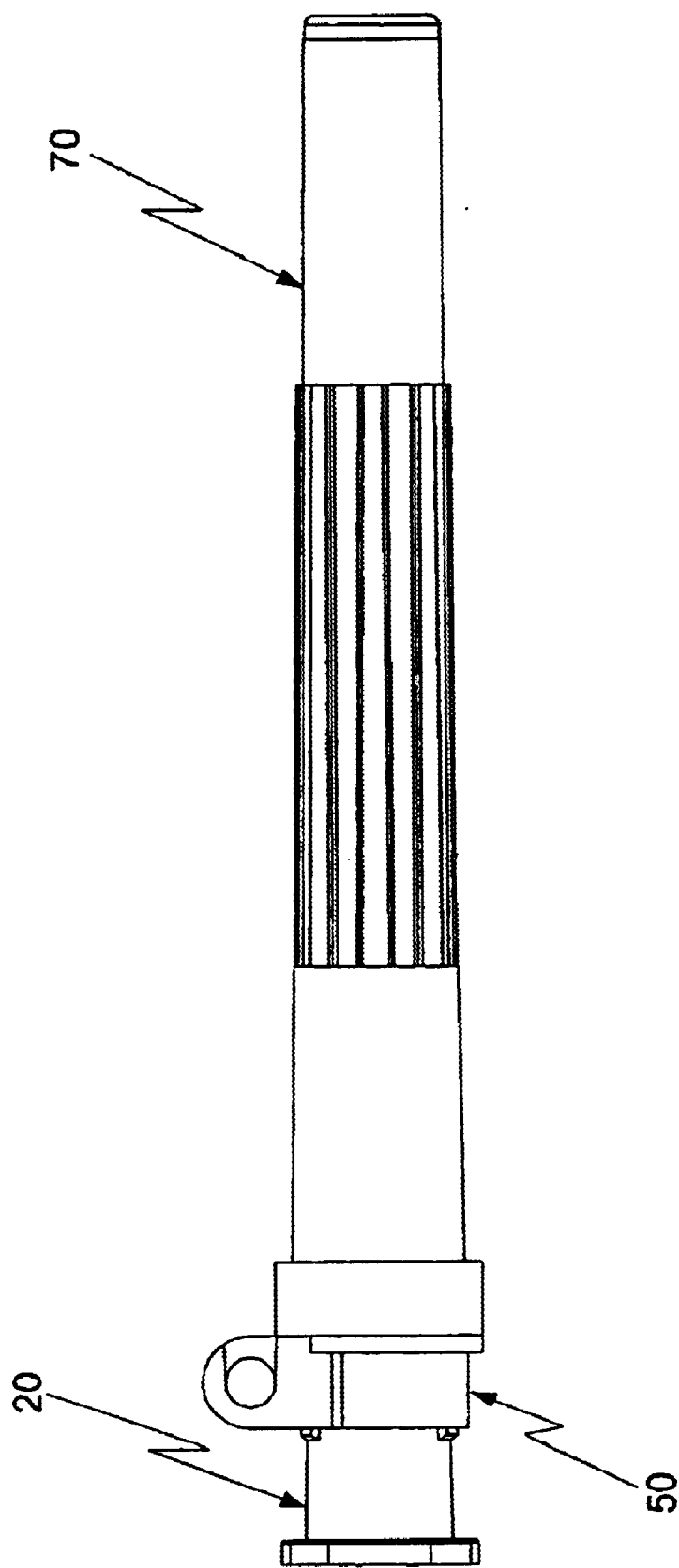

FIG. 16 illustrates another aspect of the assembly procedure, in a slightly enlarged illustration, in which the protector has been mounted on the hub in covering relation to the cannula.

Figure 17:
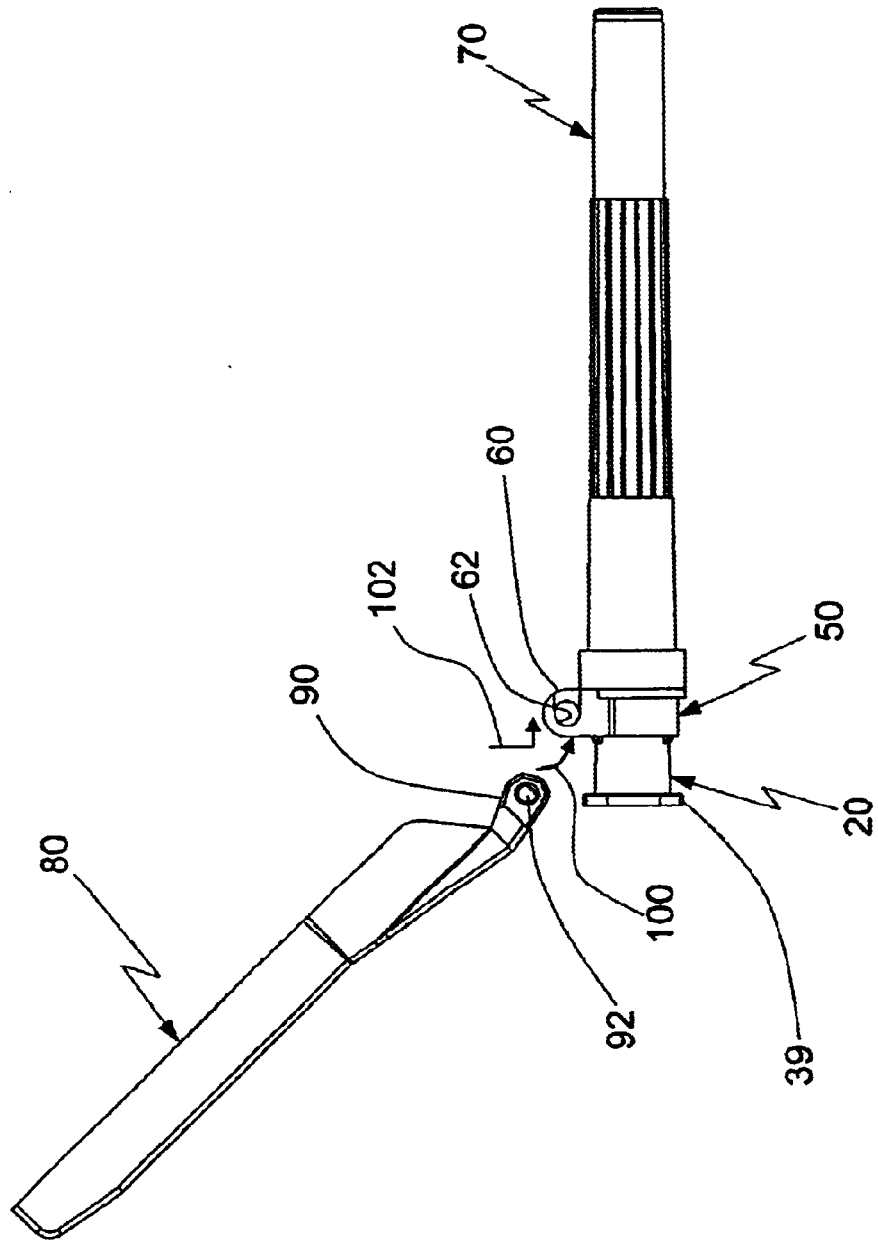

FIG. 17 generally illustrates another aspect of the assembly procedure in which the sheath is being mounted on the collar.

FIG. 18 illustrates another aspect of the assembly procedure in which the sheath has been mounted on the collar.

Figure 11:
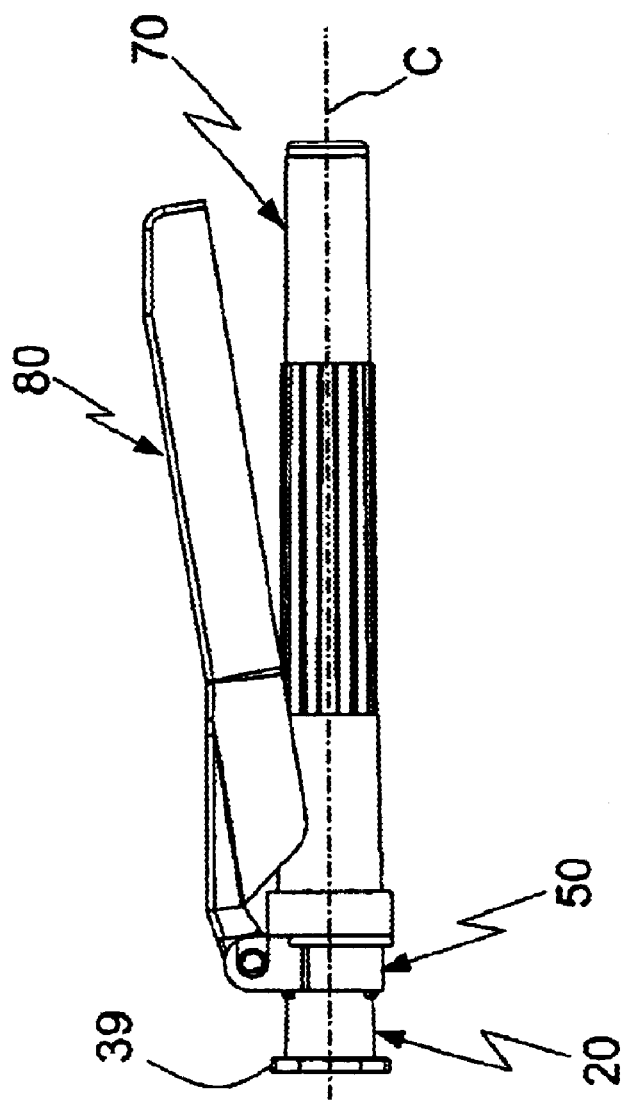
FIG. 11 is a side view of the safety needle assembly in the assembled state prior to connection to a fluid handling device such as a syringe.
Figure 19A:
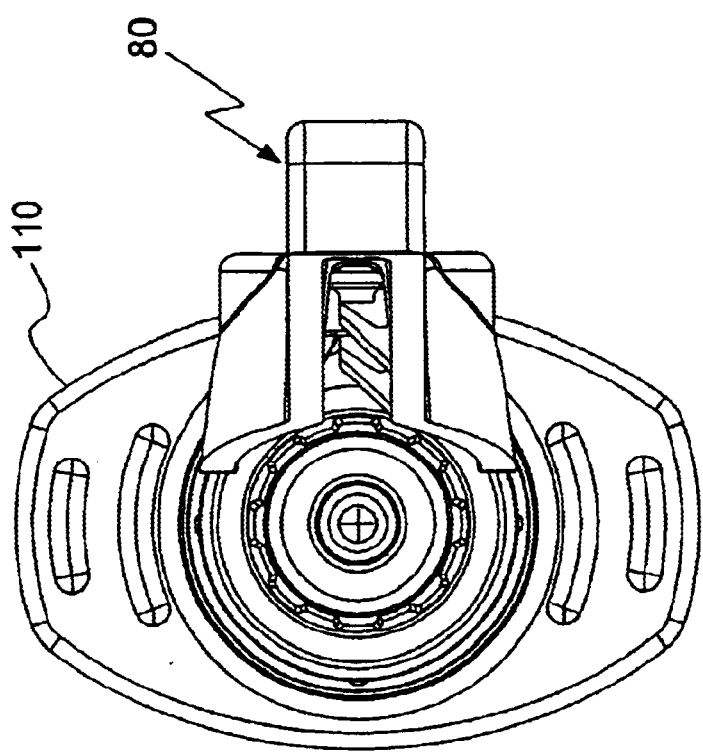

FIG. 19(a) is a rear view of the safety needle assembly shown in FIG. 11 connected to a syringe, with the sheath positioned out of alignment with the finger flange on the syringe.

Figure 19B:
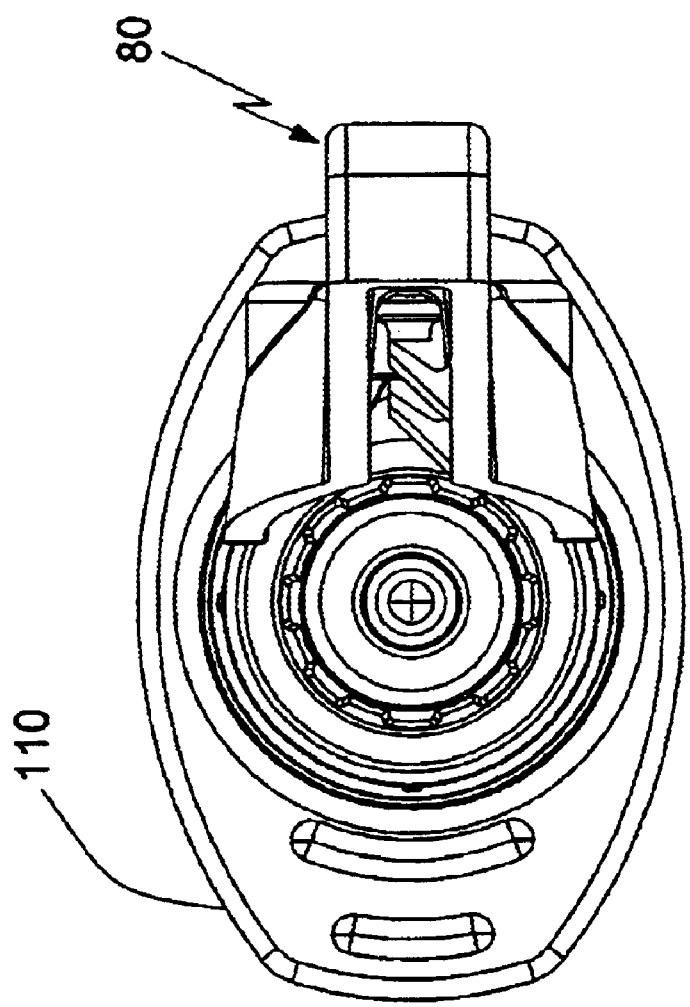

FIG. 19(b) is a rear view of the safety needle assembly shown in FIG. 11 connected to a syringe, with the sheath aligned with the finger flange on the syringe.

Figure 19C:
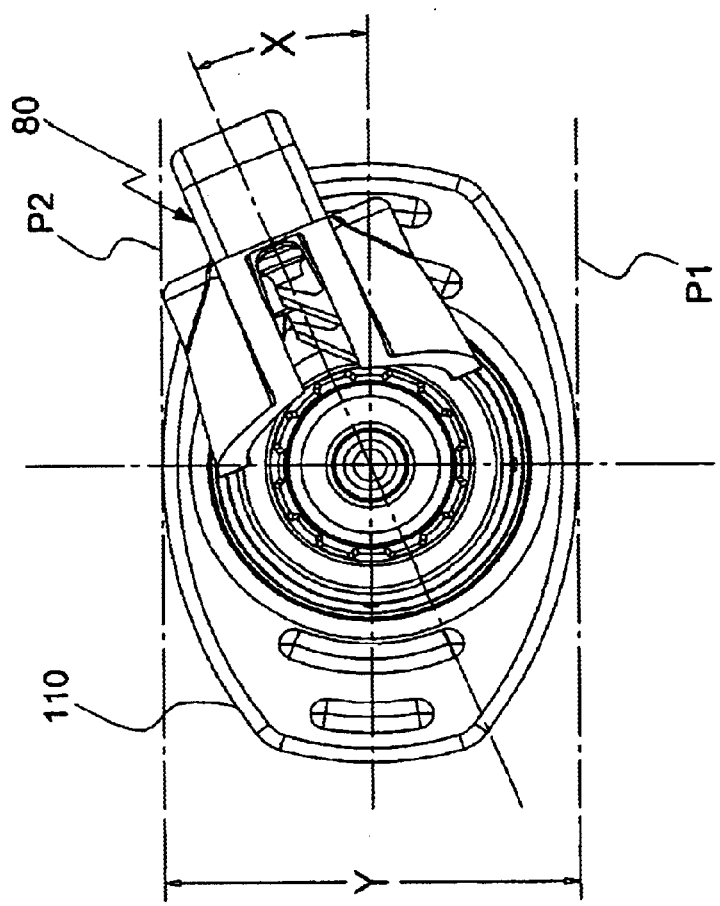

FIG. 19(c) is a rear view of the safety needle assembly shown in FIG. 11 connected to a syringe illustrating a preferred range of positioning of the sheath relative to the finger flange.

FIG. 20 is a perspective view of the safety needle assembly connected to a syringe constituting a fluid handling device.

Figure 21A:
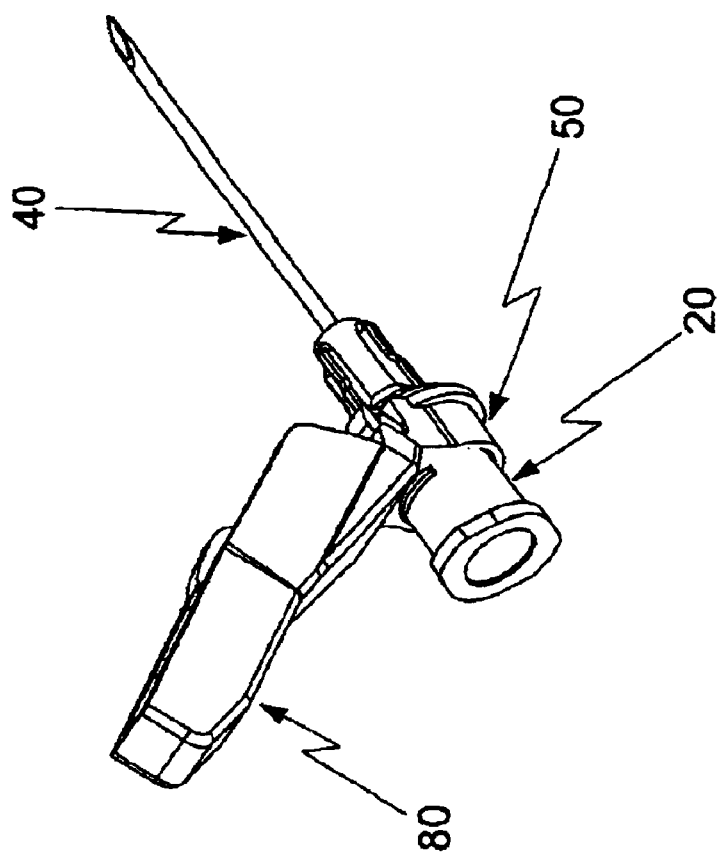

FIG. 21(a) is a perspective view of the safety needle assembly illustrating one orientation of the sheath relative to the beveled end of the cannula.

Figure 21B:
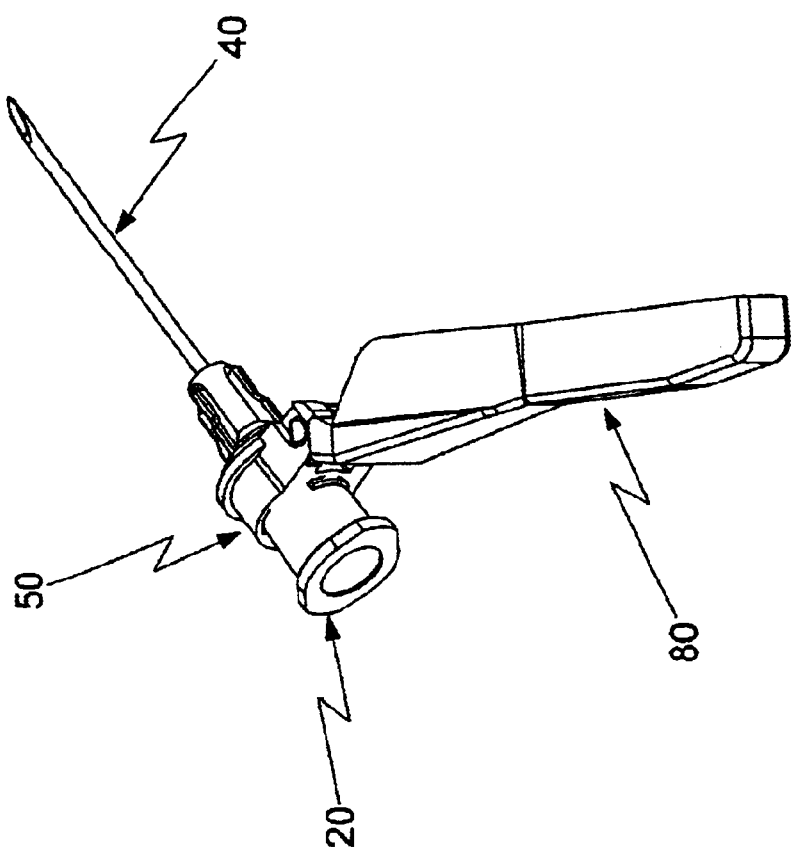

FIG. 21(b) is a perspective view of the safety needle assembly illustrating another orientation of the sheath relative to the beveled end of the cannula.

DETAILED DESCRIPTION OF THE INVENTION

The safety needle assembly according to the present invention is adapted to be connected to a fluid transfer device such as a syringe. As described below in more detail, the safety needle assembly can be packaged and later connected to the syringe or other fluid transfer device by the user, or can be connected to the syringe or other fluid transfer device and then packaged.

Figure 1:
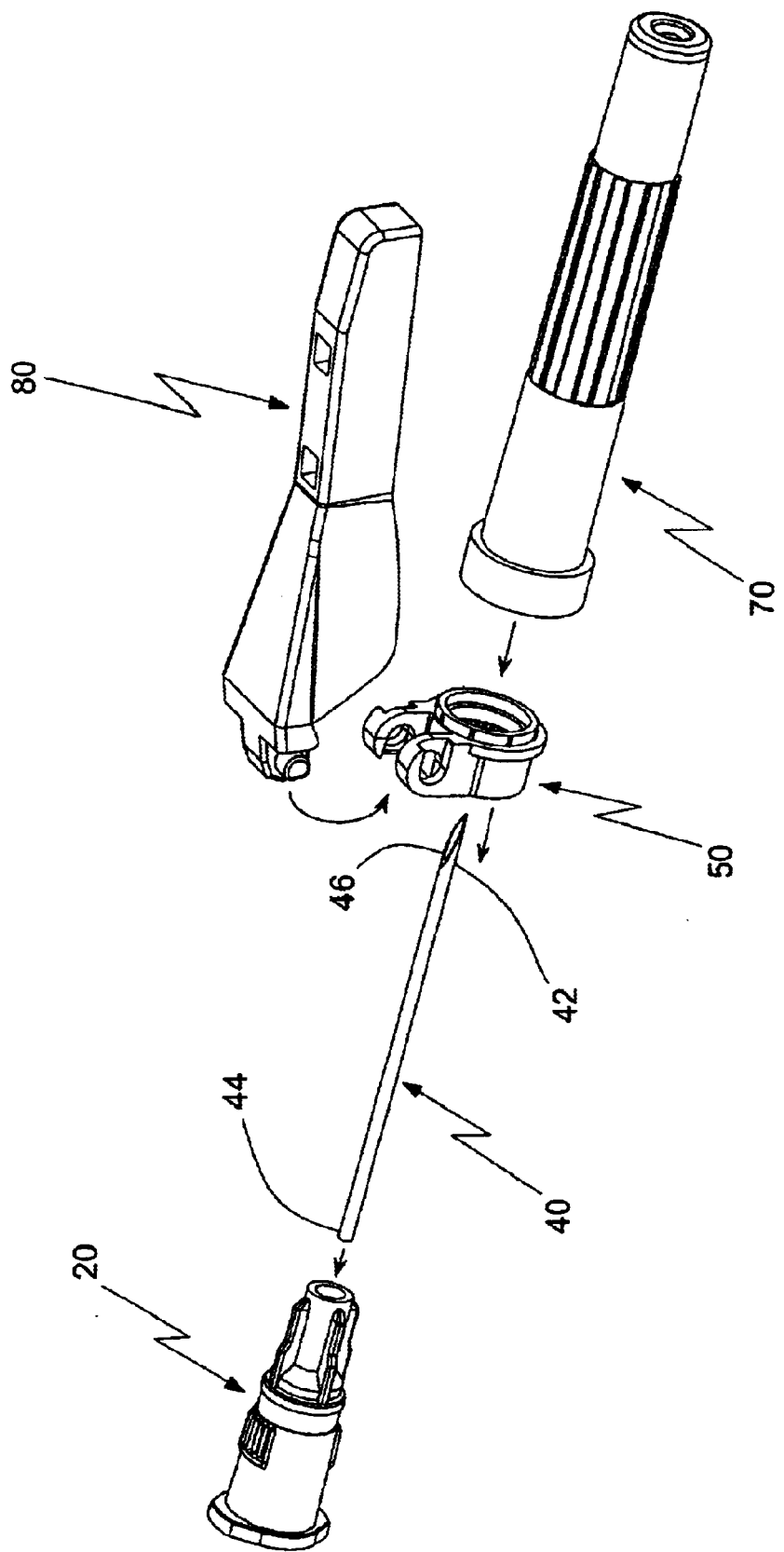
FIG. 1 is an exploded side view of the components forming the safety needle assembly of the present invention.

Referring initially to FIG. 1, the safety needle assembly includes a hub 20, a cannula 40, a collar 50, a protector 70 and a sheath 80. The cannula 40 is connected to the hub 20 in a typical manner such as through the use of an epoxy. The cannula 40 includes a proximal end portion 44 connected to the distal end of the hub 20 and a distal end portion 46 provided with a bevel to form a beveled distal end 42.

The hub 20, the collar 50, the protector 70 and the sheath 80 are preferably each formed through molding and as one-piece parts. Thus, the hub 20 including all of the features described below is formed as an integral, one-piece hub in which all of the features forming the hub are formed at the same time. Similarly, the collar 50 including all of the features described below is formed as an integral, one-piece collar in which all of the features forming the collar 50 are formed at the same time, the protector 70 including all of the features described below is formed as an integral, one-piece protector in which all of the features forming the protector are formed at the same time, and the sheath 80 including all of the features described below is formed as an integral, one-piece sheath in which all of the features forming the sheath as described below are formed at the same time, The collar 50 is adapted to be mounted on the hub 20 by moving the collar 50 over the cannula 40 and into place on the hub 20 in the manner described in more detail below. In addition, the protector 70 is adapted to be moved over the cannula 40 and positioned in covering relation to the cannula 40 so that the cannula in enclosed within the protector 70. Further, as described in more detail below, the sheath 80 is adapted to be mounted on the collar 50 in a manner that allows the sheath 80 to be pivoted relative to the collar 50.

Figure 2:
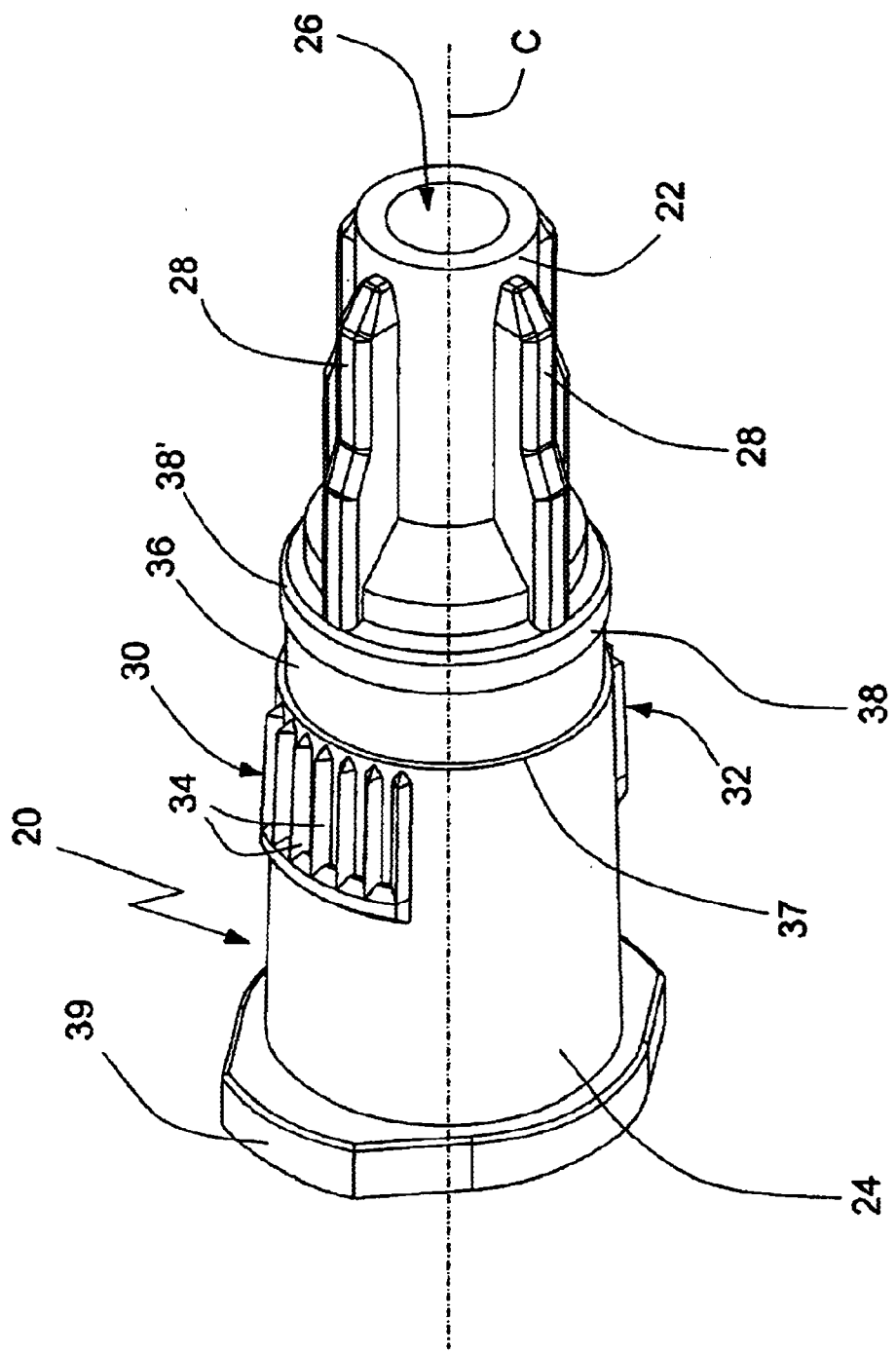
FIG. 2 is an enlarged perspective view of the hub used in the safety needle assembly shown in FIG. 1.
Figure 3:
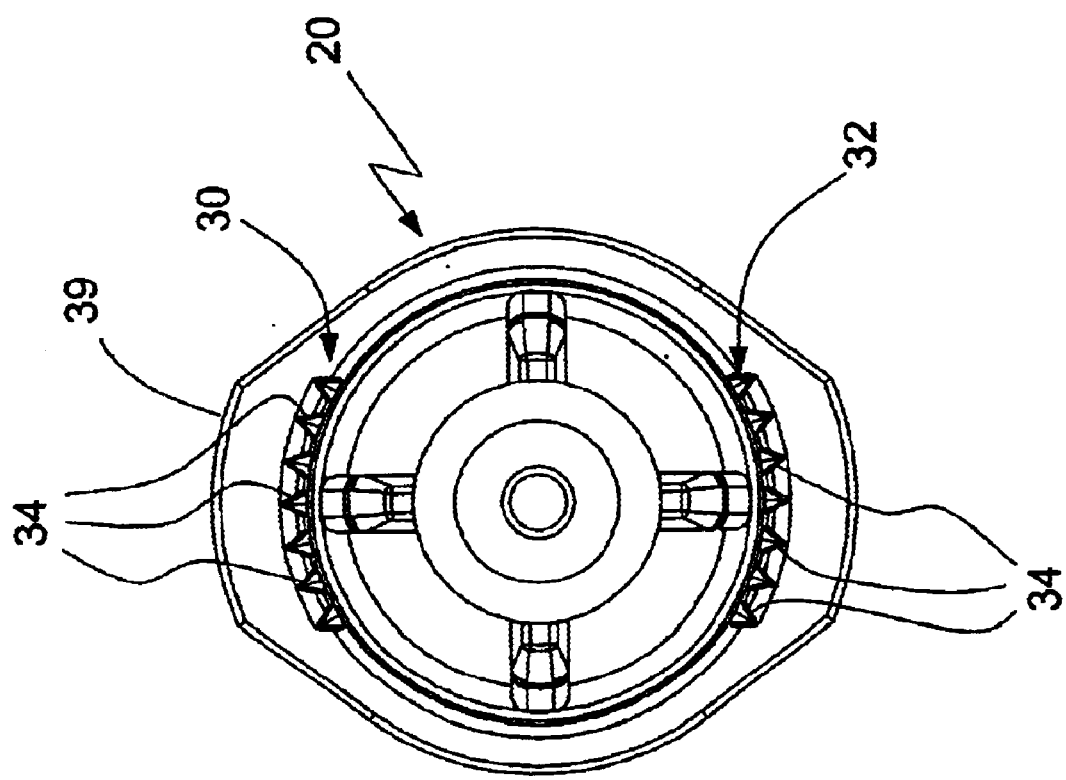
FIG. 3 is a front end view of the hub shown in FIG. 2.

As illustrated in FIGS. 2 and 3, the hub 20 includes a distal end 22 and a proximal end 24. A through hole 26 extends along the entire longitudinal extent of the hub 20, opening at both the distal end 22 of the hub 20 and the proximal end 24 of the hub 20. The proximal end portion 44 of the cannula 40 shown in FIG. 1 is fitted into the hole 26 at the distal end 22 of the hub 20 so that the lumen extending throughout the length of the cannula 40 communicates with the through hole 26 in the hub 20. As mentioned above, the distal end portion 44 of the cannula 40 is appropriately fixed to the distal end 22 of the hub 20 such as through the use of an epoxy.

The distal end portion of the hub 20 is provided with a plurality of longitudinally or axially extending ribs 28 that help facilitate centering and mounting of the collar 50 on the hub 20 in a manner described in more detail below. As can be seen in FIG. 2, the distance between the outer surface of each rib 28 and the central axis C of the hub 20 varies along the longitudinal or axial extent of each rib 28. More specifically, the distance between the outer surface of the ribs 28 and the central axis C decreases from the proximal ends of the ribs 28 towards the distal ends of the ribs 28. In the illustrated version, the distance between the outer surface of the ribs 28 and the central axis C varies in a step-wise manner.

As shown in FIGS. 2 and 3, the outer surface of the hub 20 is provided with a first set 30 of projections extending radially outwardly from the outer circumferential surface of the hub 20 and a second set 32 of projections extending radially outwardly from the outer circumferential surface of the hub 20. In the illustrated and described embodiment, each set 30, 32 of projections extends over less than one-half the outer circumferential extent of the hub 20 and are thus spaced apart from one another by a portion of the outer surface of the hub not provided with projections. Also, in the illustrated and described embodiment, the first set 30 of projections and the second set 32 of projections are positioned at diametrically opposite sides of the hub 20 and are formed as teeth or a spline 34, although the two sets of teeth need no be positioned at diametrically opposite sides of the hub. As illustrated in FIG. 2, the teeth 34 forming the first and second sets 30, 32 are located closer to the proximal end 24 of the hub 20 than the distal end 22 of the hub 20.

An annular recessed region 36 is positioned towards the distal side of the teeth 34 forming the first and second sets 30, 32 of projections. A step 38, 37 is thus formed on each axial end of the annular recessed region 36. That is, the portions 38, 37 of the hub 20 immediately adjoining the axial ends of the annular recessed region 36 each posses an outer diameter greater than the outer diameter of the annular recessed region 36.

The proximal end 24 of the hub 20 is also provided with a radially outwardly directed flange 39. This hub flange 39 is adapted to be engaged with the distal end of the fluid transfer device, for example a syringe barrel, to connect the hub 20 to the syringe barrel. This can be accomplished in a known manner such as by engaging the hub flange 39 with threads on the distal end of the syringe barrel.

Referring to FIGS. 4–7, the collar 50 is annularly shaped, having a proximal end 52 and a distal end 54. The annular collar 50 is also provided with a centrally located through-hole for allowing the collar 50 to be mounted on the hub 20. The internal surface of the collar 50 is provided with a plurality of inwardly directed projections 56. In the illustrated embodiment, the projections 56 are in the form of teeth 58 that extend around the entire inner periphery of the through-hole. As described in more detail below, the inwardly directed teeth or projections 56 are adapted to engage the two sets 30, 32 of teeth 34 on the hub 20 when the collar 50 is mounted on the hub to rotationally fix the collar 50 with respect to the hub 20.

As an alternative to the arrangement described above and illustrated in the drawing figures, the two sets of projections or teeth provided on the hub 20 can be replaced by a circumferential arrangement of projections or teeth extending around the entire circumference of the hub 20, and the circumferential arrangement of teeth or projections on the collar 50 can be replaced by two spaced apart sets of projections or teeth. As a further alternative, both the hub 20 and the collar 50 can be provided with a circumferential arrangement of projections or teeth extending around the entire circumference of the hub and collar.

The inner surface of the annular collar 50 is also provided with an inwardly directed annular ridge 57. This annular ridge 57 also extends around the entire inner periphery of the through-hole in the annular collar 50 and is adapted to be seated in the annular recessed region 36 on the hub 20 when the collar 50 is mounted on the hub 20. Although the radially inwardly directed annular ridge 57 is illustrated as a continuous uninterrupted annular ridge, it is also possible to form the annular ridge as a plurality of separated segments, each extending along a portion of the inner circumference of the collar 50.

The inwardly extending ridge 57 possesses an internal diameter that is less than the outer diameter of the two step portions 38, 37 of the hub 20 immediately adjoining the recessed region 36. The inner diameter of the inwardly extending ridge 57 can be equal to, slightly greater than or slightly less than the outer diameter of the recessed region 36 on the hub 20.

The annular collar 50 is also provided with a pair of spaced apart and outwardly directed sheath mounting ears 60. These sheath mounting ears 60 provide a part of the mechanism for pivotally or hingedly connecting the sheath 80 to the collar 50 so that the sheath 80 can pivot relative to the collar 50, as well as the cannula and hub.

Figure 6:
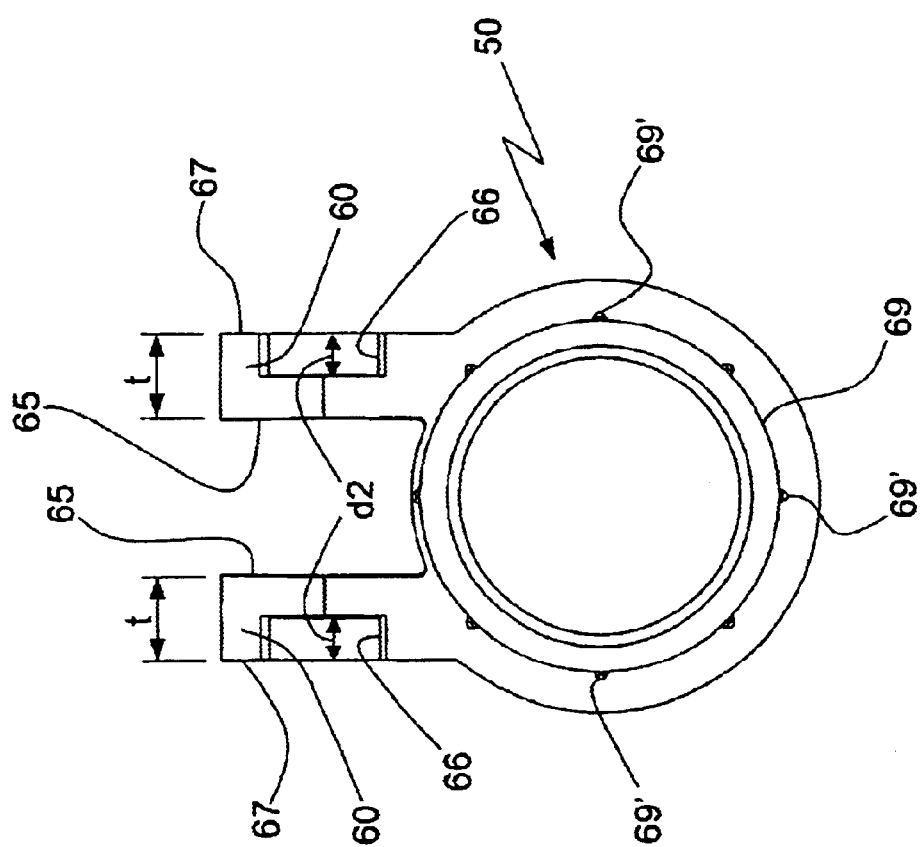
FIG. 6 is a front end view of the collar shown in FIG. 4.

Each of the mounting ears 60 includes a distal end 61 and proximal end 63. Further, each of the mounting ears 60 is provided with a first side surface 65 forming an inner side surface and a second side surface 67 forming an outer side surface. The first side surfaces or inner side surfaces 65, 65 of the two mounting ears 60 face towards one another. Thus, as seen in FIG. 6, each of the mounting ears 60 possesses a thickness t represented by the distance between the first and second side surfaces 65, 67. In addition, each of the mounting ears 60 possesses a width w represented by the distance between the proximal end 63 and the distal end 61 of the mounting ears 60.

Each of the mounting ears 60 is provided with a through hole 62. The through-hole 62 in each of the mounting ears 60 is formed by virtue of a first groove 64 provided at the inner side surface 65 of each mounting ear 60 and a second groove 66 provided at the outer side surface 67 of each mounting ear 60.

Described in more detail, the first grooves 64 formed at the inner side surface 65 of each mounting ear 60 extends from the proximal end 63 of the mounting ear 60 towards the distal end 61 of the mounting ear. The first grooves 64 open to the proximal end 63 of the mounting ears 60, but stop short of the distal end 61 of the mounting ears 60. The second grooves 66 formed at the outer side surface 67 of each mounting ear 60 extends from the distal end 61 of the mounting ear towards the proximal end 63 of the mounting ear 60. The second grooves 66 open to the distal end of the mounting ear 60, but stop short of the proximal end 63 of the mounting ear 60. As can be seen from FIG. 4, the first and second grooves 64, 66 on each of the mounting ears 60 overlap one another with respect to the width-wise extent of the mounting ears 60.

The length of the first and second groove 64, 66 (i.e., the dimension of the grooves 64, 66 in the width-wise direction of the mounting ears 60) in conjunction with the depth d1, d2 of the first and second grooves 64, 66 (i.e., the dimension of the grooves 64, 66 in the thickness direction of the mounting ears 60) are specifically selected so that in the region of overlap of the first and second grooves 64, 66, the respective through-holes 62 are formed.

The combined depth (d1+d2) of the first and second grooves 64, 66 on each of the mounting ears 60 is at least equal to the thickness t of the respective mounting ears 60, and is preferably slightly greater than the thickness t of the respective mounting ears 60. In this way, with the overlap of the first and second grooves 64, 66 in the width-wise direction of the mounting ears 60 as shown in FIG. 4, the through-holes 62 are automatically formed.

In the illustrated and described embodiment, the depth d1, d2 of the first and second grooves 64 in one mounting ear 60 are equal to one another, with each of the depths d1, d2 being at least equal to, and preferably slightly greater, than one-half the thickness t of the mounting ear 60. Similarly, the depth d1, d2 of the first and second grooves 64, 66 in the other mounting ear 60 are also equal to one another, with each of the depths d1, d2 being at least equal to, and preferably slightly greater, than one-half the thickness t of the mounting ear 60. Of course, the first and second grooves 64, 66 in each mounting ear 60 need not be equal to one another.

The combined length of the first and second grooves 64, 66 in the width-wise direction in each mounting ear 60 is greater than the width w of the respective mounting ear 60. In the illustrated and described embodiment, the length of each of the first and second grooves 64, 66 in each mounting ear 60 is greater than one-half the width w of the respective mounting ear 60 so that the first and second groove 64, 66 overlap one another as described above. By virtue of the configuration and arrangement of the grooves 64, 66 as described above, the through-hole 62 in each mounting ear 60 can be formed in a mold that is appropriately configured to form the grooves 64, 66 in each of the mounting ears 60. A more complicated mold configuration for forming the through-holes 62 is thus not required.

Figure 4:
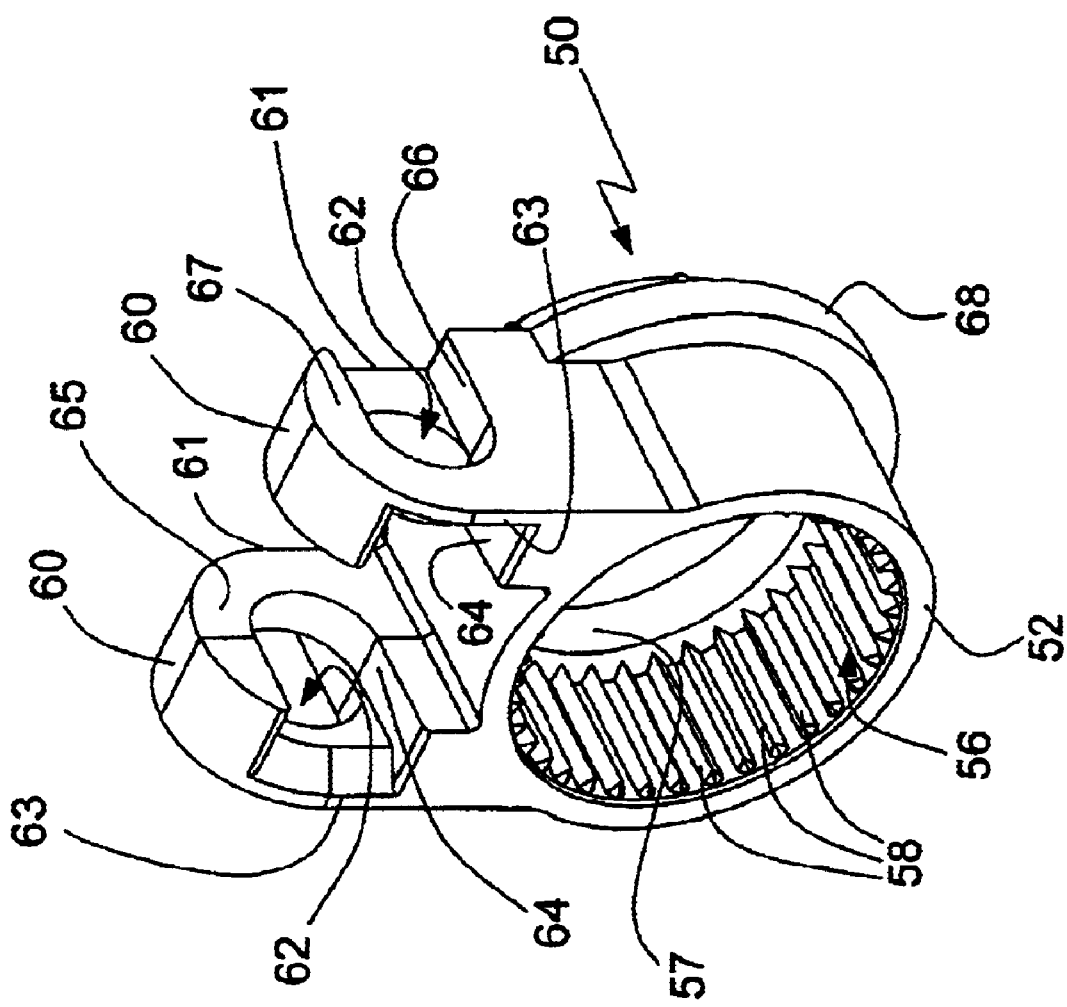
FIG. 4 is an enlarged rear perspective view of the collar used in the safety needle assembly shown in FIG. 1
Figure 5:
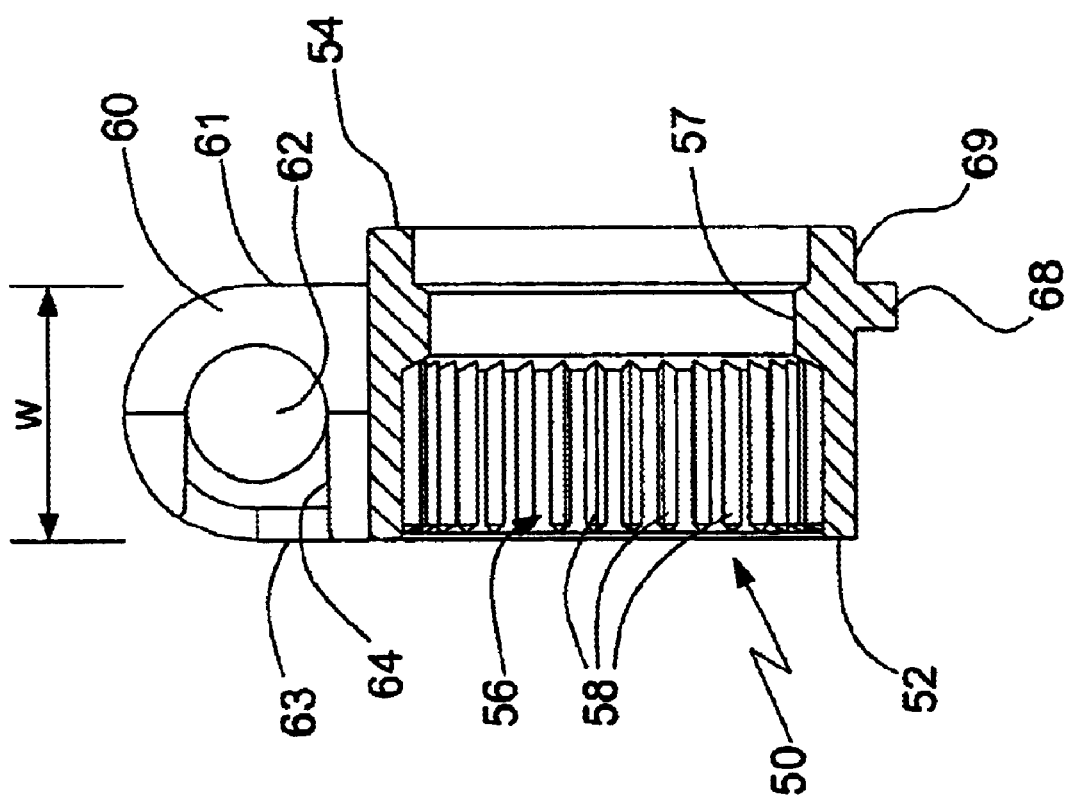
FIG. 5 is a cross-sectional view of the collar shown in FIG. 4.

As seen in FIGS. 4 and 5, the collar 50 is also provided with a radially outwardly directed annular ridge 68. This annular ridge 68 is located adjacent the distal end portion of the collar 50, but is spaced towards the proximal end 52 of the collar from the distal end 54. This thus defines a seating surface 69 which, as described in more detail below, is used to seat or mount the protector 70. A plurality of spaced apart protuberances 69' are disposed along the circumferential extent of the seating surface 69 to help facilitate mounting or seating of the protector 70 on the seating region 69. In addition, the annular ridge 68 forms a stop which engages the proximal end of the protector 70 when the protector is mounted on the seating region 69 of the collar 50.

Figure 8:
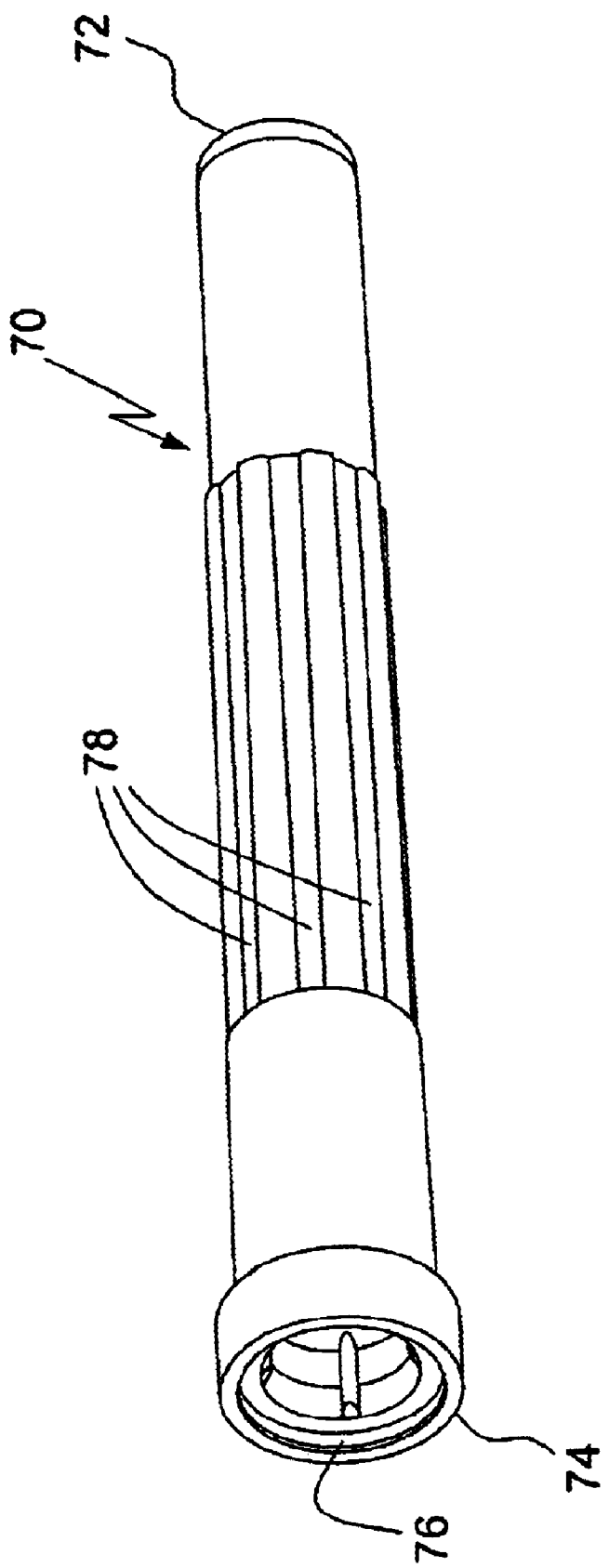
FIG. 8 is an enlarged perspective view of the protector used in the safety needle assembly shown in FIG. 1.

As shown in FIG. 8, the protector 70 is formed as an elongated cylindrical hollow member having a distal end 72 and a proximal end 74. The protector 70 is open at the proximal end 74 and preferably closed at the distal end 72. An intermediate portion of the exterior surface of the protector 70 can be provided with longitudinal ribs 78 to facilitate gripping by the user. The interior of the protector 70 at the proximal end 74 is provided with a seating surface 76. When the protector 70 is positioned over the cannula 40 upon assembly, the seating surface 76 of the protector 70 encircles the seating region 69 on the collar 50 and engages the protuberances 69'. In addition, the proximal end 74 of the protector contacts the annular ridge 68.

Figure 9:
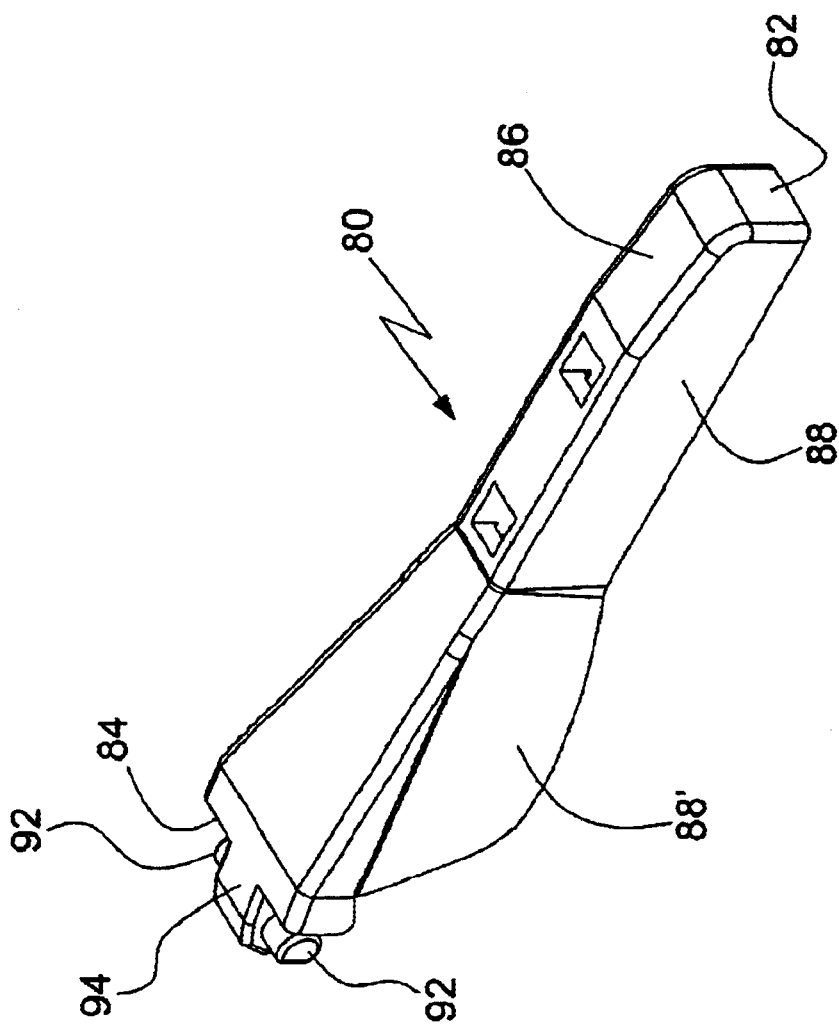
FIG. 9 is an enlarged top perspective view of the sheath forming a part of the safety needle assembly shown in FIG. 1.
Figure 10:
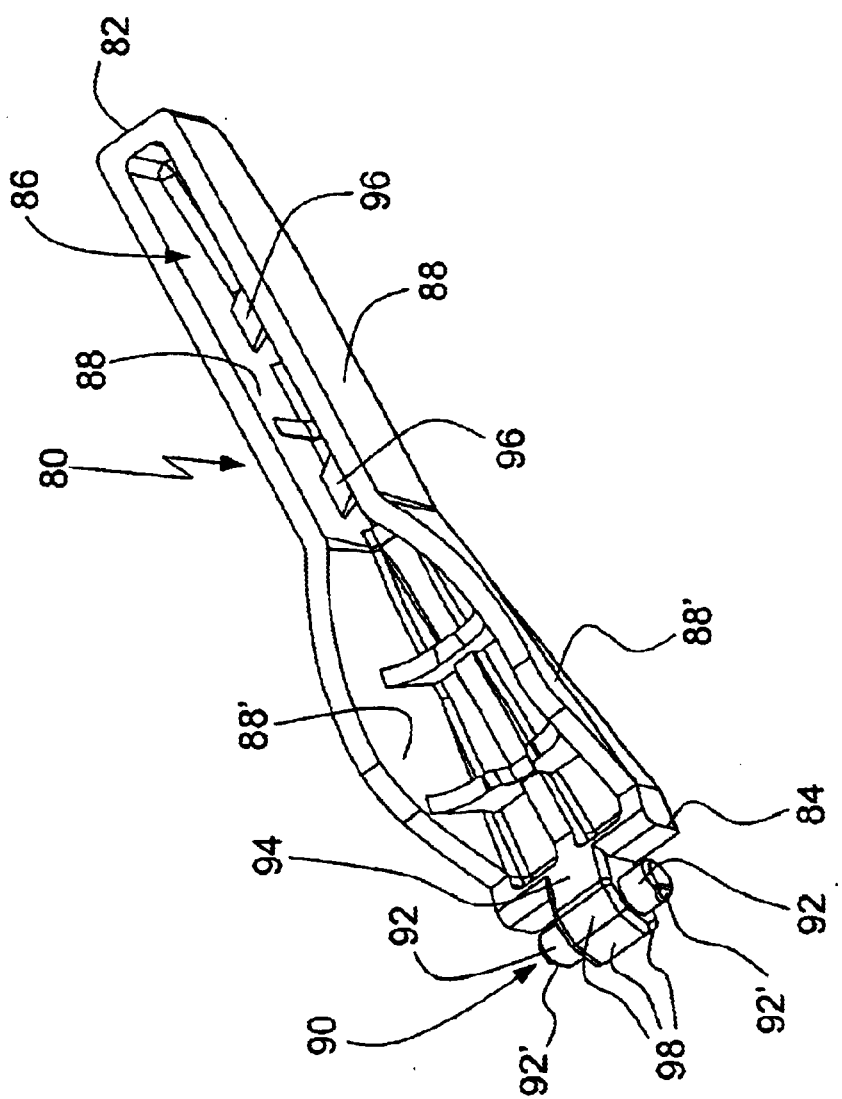
FIG. 10 is a bottom perspective view of the sheath shown in FIG. 9.

Referring to FIGS. 9 and 10, the sheath 80 is formed as a generally elongated member having a distal end 82 and a proximal end 84. The sheath 80 is provided with an opening 86 that extends along at least a portion of the longitudinal extent of the sheath 80 and communicates with the interior of the sheath 80. During use or operation of the safety needle assembly, as the sheath 80 is pivoted towards the cannula 40 (shown in FIG. 1), the cannula is adapted to pass through the opening 86 in the sheath and into the interior of the sheath 80. In the illustrated and described embodiment, the opening 86 in the sheath 80 extends along the entire longitudinal extent of the sheath 80 so that the sheath is completely open along one side.

The sheath 80 possesses a back wall 86 and two oppositely positioned side walls 88. The opening 86 in the sheath 80 is defined at the side of the sheath 80 opposite the back wall 86.

As further illustrated in FIGS. 9 and 10, the proximal portion 88' of each of the side walls 88 of the sheath 80 flare outwardly or are angled outwardly relative to the distal portion of the sidewall. This arrangement makes it possible to position the sheath 80 closer to the protector 70, when the protector 70 is in covering relation to the cannula, than would otherwise be the case if the sidewalls 88 were not flared or angled outwardly.

The sheath 80 includes a collar connecting mechanism 90 located at the proximal end of the sheath 80. This collar mounting mechanism 90 includes a pair of pins 92 extending in opposite directions from a pin mount 94. As described in more detail below, each of the pins 92 is adapted to be positioned in the through-hole 62 in one of the mounting ears 60 to pivotally mount or connect the sheath 80 on the collar 50. As shown in FIG. 10, the pins 92 are provided with beveled edges 92' that help facilitate mounting the pins 92 in the through-holes 62 of the mounting ears 60.

FIG. 10 also illustrates that the pin mount 94 is provided with a plurality of flat surfaces 98. As described in more detail below, these flat surfaces 98 are adapted to engage the portion of the outer surface of the collar 50 located between the mounting ears 60 during pivoting movement of the sheath 80. This produces a desirable clicking feeling when the sheath 80 is pivoted towards the cannula.

The interior of the sheath 80 is provided with one or more locking tabs 96 formed by punching through portions of the back wall 86 of the sheath 80 as shown in FIG. 9. These locking tabs 96 are able to flex when engaged by the cannula as sheath 80 is being pivoted towards the cannula 40 (shown in FIG. 1). The cannula is thus able to move past the tabs 96. Once the cannula has moved past the tabs 96, the cannula is prevented from moving back out of the interior of the sheath 80. The cannula is thus permanently locked within the interior of the sheath 80. This locking occurs automatically in that the movement of the cannula into the interior of the sheath 80 and past the locking tabs 96 is all that is necessary to permanently lock the cannula within the interior of the sheath 80.

In its assembled state, the safety needle assembly includes the cannula 40 shown in FIG. 1 connected to the distal end 22 of the hub 20 so that the cannula is fixed relative to the hub. In addition, the collar 50 is mounted on the hub 20 so that the inwardly directed ridge 57 on the collar 50 is positioned in the recessed region 36 of the hub. At the same time, the teeth 58 on the interior of the collar 50 engage the two sets 30, 32 of teeth 34 on the hub 20 to thus rotationally fix the collar 50 with respect to the hub 20. Also, the protector 70 is removably positioned in covering relation to the cannula 40 so that the proximal end 74 of the protector 70 encircles the seating region 69 on the distal end of the collar 50, with the interior seating surface 76 on the protector 70 engaging the protuberances 69' at the seating region 69. Further, the sheath 80 is connected to the collar 50 by virtue of the pins 92 on the sheath 80 being positioned in the through holes 62 in the mounting ears 60 of the collar 50. The assembled state of the safety needle assembly is shown in FIG. 11. As can be seen, the sheath 80 is positioned in close contacting relation to the protector 70 so that the sheath 80 is located as close as possible to the central axis C of the cannula.

As mentioned previously, the safety needle assembly shown in FIG. 11 can be attached to a fluid handling device such as a syringe by the manufacturer and then subsequently packaged for sale to the user. Alternatively, the safety needle assembly can be packaged for sale to the user in the assembled state shown in FIG. 11, whereupon the user would attach the safety needle assembly to a fluid handling device such as a syringe. In either case, with the assembled safety needle attached to the fluid handling device, the safety needle assembly is used in the following manner.

Figure 12:
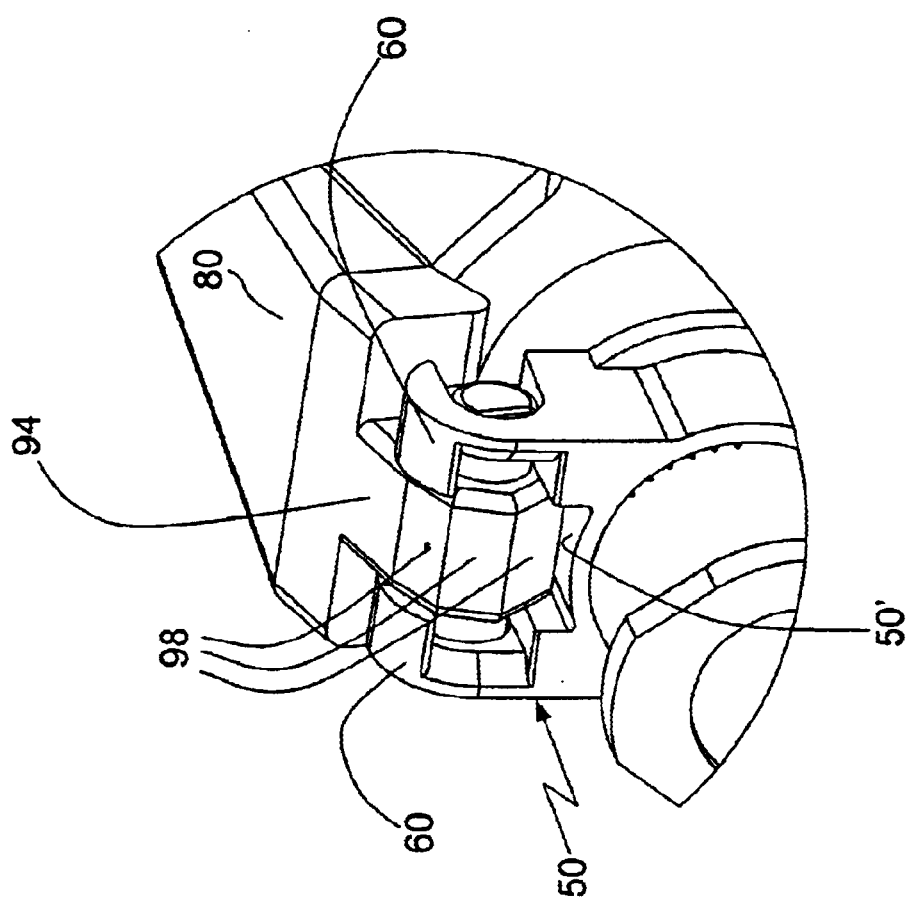
FIG. 12 is an enlarged view of a portion of the needle assembly illustrating flat surfaces on the sheath that engage a portion of the collar during pivoting movement of the sheath.

The user can initially pivot the sheath 80 away from the protector 70 to allow the protector 70 to be removed. During pivoting movement of the sheath 80, the flat surfaces 98 on the pin mount 94 of the sheath 80 engage the portion 50' of the outer surface of the collar 50 located between the mounting ears 60 as shown in detail in FIG. 12. This produces a clicking feeling to the user. In addition, the engagement of the flat surfaces 98 with the portion of the collar helps maintain the sheath 80 in the desired position. That is, the engagement of the flat surfaces 98 with the portion of the collar 50 inhibits the sheath 80 from pivoting on its own and so the sheath is not likely to interfere with the use of the cannula.

After pivoting the sheath 80 out of the way, the protector 70 is removed to expose the cannula 40 shown in FIG. 1. Once the protector 70 is removed, the user can use the cannula in the desired manner, for example to gain access to a patient's blood vessel. After the user has finished using the cannula, the sheath 80 is pivoted towards the cannula 40 (i.e., towards the closed or covering position) to safe the cannula. As the sheath 80 is pivoted towards the cannula, the engagement of the flat surfaces 98 on the pin mount 94 with the portion 50' of the outer surface of the collar 50 located between the mounting ears once again results in a clicking feeling to the user so the user feels as though they have more control over the pivoting movement of the sheath 80. The sheath 80 continues to be pivoted towards the cannula 40 by the user until the cannula pushes past the locking tabs 96 and is permanently and automatically locked in place within the interior of the sheath 80 by the locking tabs. At this point, the cannula 40 is completely covered by the sheath. Further, the cannula cannot move back past the locking tabs 96 and so the cannula (including the beveled distal end) is considered to be safe. It is possible to configure and dimension the flat surfaces 98 on the pin mount of the sheath 80 so that as the sheath 80 is pivoted towards the closed position, if the pushing force applied to the sheath is removed (e.g., the user stops pivoting the sheath) at a point in which the sheath 80 is not pivoted sufficiently to cause the cannula to be locked behind the locking tabs 96, the flat surfaces 98 will cause the sheath to pivot backward away from the cannula, thus providing an immediate indication that the sheath 80 has not been sufficiently pivoted towards the closed position to cause the cannula to be engaged behind the locking tabs 96.

The description provide above generally describes how the safety needle assembly is assembled. A more detailed description of this assembly procedure is set forth below. As an initial step, the proximal end of the cannula 40 is fitted into the through hole 26 at the distal end 22 of the hub 20. The cannula 40 is then fixed in place relative to the hub 20 in a typical manner such as through use of epoxy which may be subsequently heated to set the epoxy and firmly fix the cannula 40 in the hub 20. The resulting hub and attached cannula are shown in the left side of FIG. 13.

Figure 13:
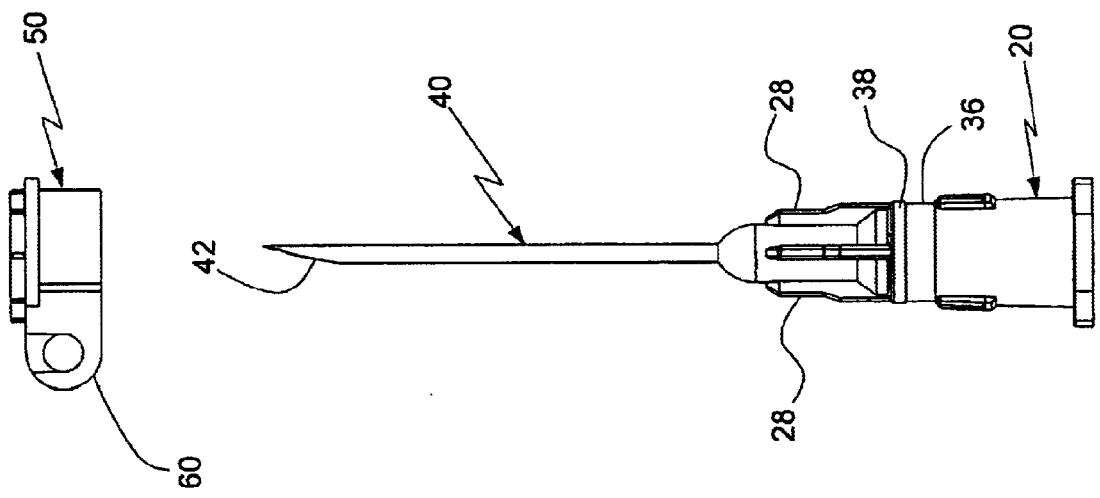
FIG. 13 illustrates one aspect of the assembly procedure in which the cannula has been attached to the hub prior to mounting the collar on the hub.

According to one possibility, the next step involves mounting the collar 50 on the hub 20 as generally depicted in FIG. 13. This can be accomplished by, for example, vertically orienting the hub 20 and dropping the collar 50 onto the hub 20 from the distal end of the hub 20. Here, the ribs 28 on the distal end portion of the hub 20 help guide and center the collar 50 on the hub 20 as the collar is released. Of course, it is not necessary to vertically orient the hub 20 to position to the collar 50 on the hub 20.

At this point, it is desirable to orient the collar 50 in a particular position with respect to the cannula, particularly the beveled distal end 42 of the cannula 40. The reason is because it is expected that some users of the safety needle assembly will want the sheath 80 to be oriented in one of two positions relative to the bevel 42 at the distal end 46 of the cannula 40. One desirable orientation involves the sheath 80 being oriented relative to the bevel 42 at the distal end 46 of the cannula so that with the cannula 40 oriented horizontally and the bevel 42 on the distal end of the cannula facing directly upward, the sheath 80 is able to pivot in a vertical plane. This orientation is shown in FIG. 21(a). The other desirable orientation is 90° to the orientation described above. That is, with the cannula 40 positioned horizontally and the bevel 42 on the distal end 46 of the cannula facing directly upward, the sheath 80 is able to pivot in a horizontal plane. This alternative orientation of the sheath relative to the bevel is illustrated in FIG. 21(b). Depending upon the particular preferences of the user and perhaps the particular procedure with which the safety needle assemble is being used, users may prefer one of these orientations over the other so that the sheath 80 does not interfere with the desired usage. Depending upon the preferences of the user and the procedure for which the needle assembly is being used, one of these two orientations of the sheath relative to the cannula bevel may be preferred and desired.

There is thus an interest in properly orienting the collar 50 relative to the cannula, particularly the beveled end 42 of the cannula 40, to ensure that the sheath 80 is oriented in one of the two positions mentioned above relative to the bevel end 42 of the cannula 40. Thus, once the collar 50 is placed on the hub 20, it is necessary to be able to rotate the collar 50 to the desired relative position before the collar 50 is rotationally fixed on the hub the trough engagement of the teeth 34 on the outer surface of the hub 20 and the teeth 58 on the interior of the collar 50. For this reason, the inner diameter of the inwardly directed ridge 57 on the collar 50 possesses a diameter smaller than the outer diameter at the step 38 located at the distal side of the recessed region 36. With this relationship, when the collar 50 is placed on the hub 20 such as in the manner described above, the inwardly directed annular ridge 57 on the interior collar 50 contacts the end surface 38' of the step 38 shown in FIG. 2. The collar 50 is thus unable to move any further along the hub 20 in the absence of an additional applied force. However, the collar 50 is free to be rotated relative to the hub 20.

With the collar 50 positioned in this manner relative to the hub 20, the location or facing direction of the bevel 42 on the distal end 46 of the cannula 40 is identified. Preferably the collar 50 (or perhaps the hub, or both) is then rotated to the appropriate position to ensure that when the sheath is mounted on the collar, the sheath 80 is oriented relative to the bevel 42 on the cannula at one of the two positions mentioned above. Thus, the collar 50 is rotated to position the sheath mounting portion 90 of the collar 50 at the position which will achieve such orientation when the sheath 80 is mounted on the sheath mounting portion 90 of the collar 50. The orientation of the cannula bevel 42 or the direction in which the cannula bevel 42 is facing can be determined using known types of equipment.

Figure 14:
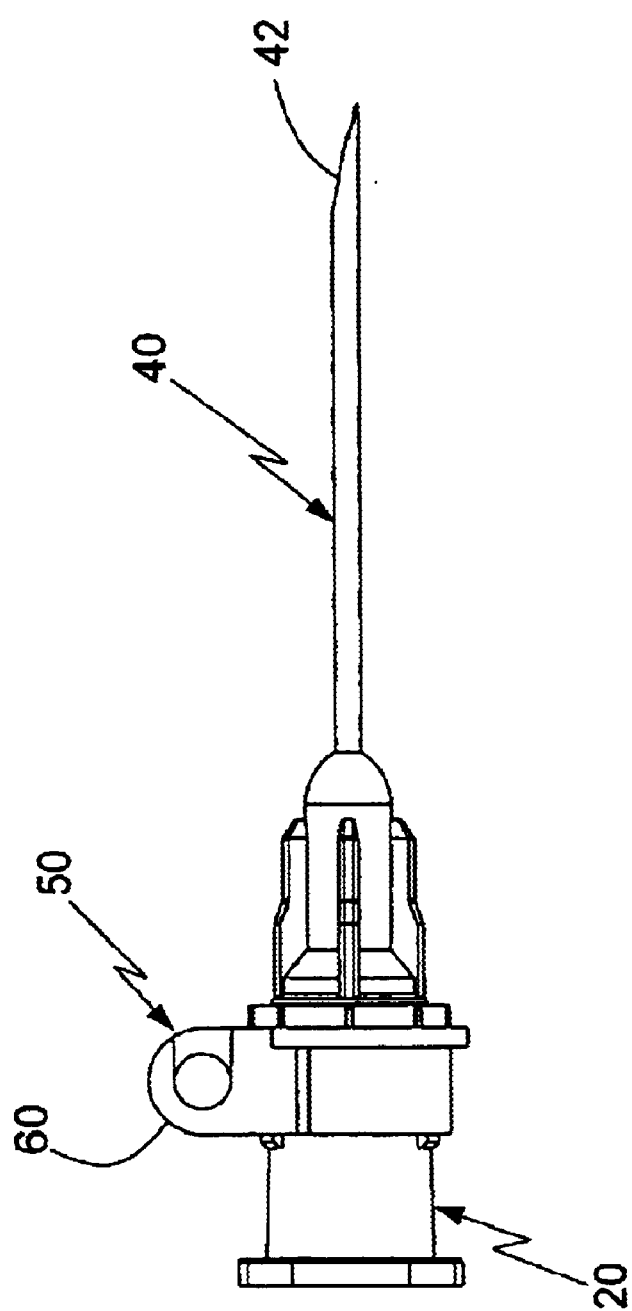
FIG. 14 illustrates another aspect of the assembly procedure in which mutual rotation of the collar and the hub has been effected to orient the collar relative to the bevel on the cannula at a desired orientation, and the collar has been pushed onto the hub.

Once the collar 50 has been oriented in the proper position relative to the hub 20, an axial force is applied to the collar and/or the hub 20 to cause the collar 50 to move the towards the proximal end 24 of the hub. The applied force is sufficient to cause the annular ridge 57 on the collar to move over the step 38 on the hub 20. The annular ridge 57 then moves into the annular recessed region 36 of the hub 20 and is prevented from moving further towards the proximal end of the hub 20 by virtue of the step 37 on the proximal side of the annular recessed region 36. In addition, once the annular ridge 57 is located in the annular recessed region 36, the collar 50 cannot be removed from the hub towards the distal end 22 of the hub by virtue of the step 38 positioned on the distal side of the annular recessed region 36. When the annular ridge 57 of the collar 50 is positioned in the annular recessed region 36, the two sets 30, 32 of teeth 30 on the hub 20 engage the teeth 58 on the inner periphery of the collar 50. This meshing engagement of the teeth rotationally fixes the collar 50 relative to the hub 20 so that the collar 50 and the hub 20 cannot be rotated relative to one another. The collar 50 positioned on the hub 20 in one of the two desired orientations described above (i.e., the orientation in which, when the cannula 40 is oriented horizontally and the bevel 42 on the distal end of the cannula faces directly upward, the sheath 80 is able to pivot in a vertical plane) is shown in FIG. 14.

The next step in the assembly process is to position the protector 70 in covering relation to the cannular as generally shown in FIG. 15. This can be accomplished by simply placing the protector 70 over the cannula to cover the sharp bevel 42 at the distal end of the cannula 40. In the illustrated and described embodiment of the safety needle assembly, the proximal end 74 of the protector 70 is mounted on the collar 50. More particularly, as described above, the seating surface 76 at the proximal end 74 of the protector 70 surrounds the seating region 69 at the distal end of the collar 50 and engages the protuberances 69' located at the seating region 69. Also, the protector 70 is mounted on the collar 50 so that the proximal end 74 of the protector 70 contacts or engages the annular ridge or stop 68 on the collar 50. Further, the interior surface of the protector 70 can be provided with an inward step at a position spaced a short distance from the proximal end 74 of the protector 70. This inward step forms a smaller inner diameter portion of the protector 70 that is of a dimension allowing the inner surface of the protector to frictionally engage the distal ends of the ribs 28 as the protector 70 is mounted on the hub 20. The protector 70 can thus be mounted on and engage the collar 50 as well as the hub 20. FIG. 16 illustrates the protector after it has been mounted on the hub and collar in covering relation to the cannula.

Figure 7:
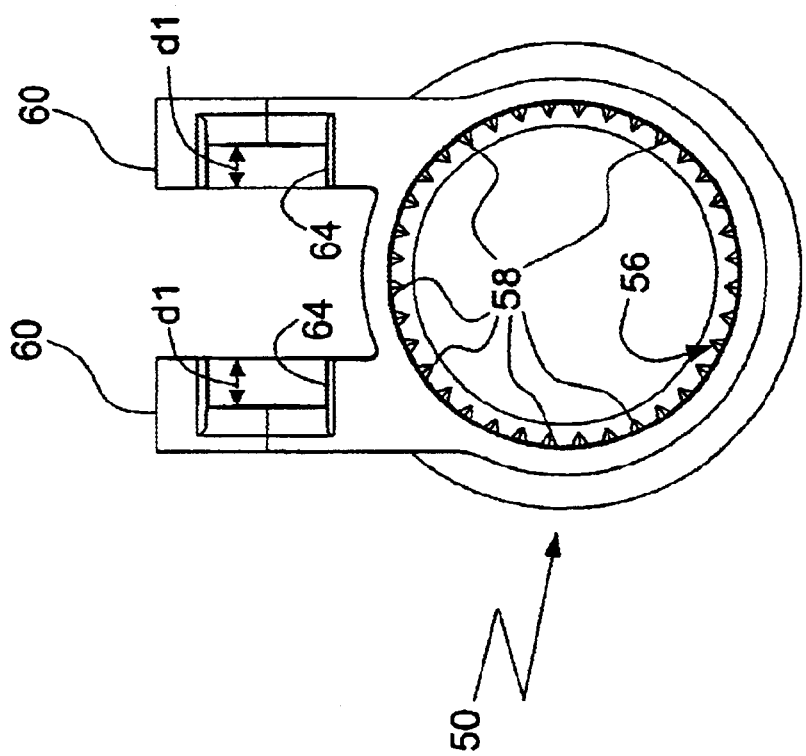
FIG. 7 is a rear end view of the collar shown in FIG. 4

As generally shown in FIG. 7, the next step involves mounting the sheath 80 on the collar 50 by connecting the collar connecting mechanism 90 of then sheath 90 to the mounting ears 60 of the collar 50. This can be accomplished in a variety of ways. In one preferred form, the sheath 80 is moved in one motion along an arcuate path of movement as shown by the arrow 100 in FIG. 17 to position the pins 92 of the sheath 80 in the through holes 62 of the mounting ears 60. With this type of movement, the hub flange 39 may interfere with the mounting movement of the sheath 80. Thus, as an alternative, the sheath 80 can be mounted on the collar 50 through use of two movements represented by the arrow 102 in FIG. 17. Here, the sheath 80 is first moved towards the collar 50 in a direction perpendicular to the longitudinal extent of the assembly (i.e., downward in FIG. 17) and is then moved towards the mounting ears 60 (i.e., towards the right in FIG. 17).

In either alternative, the sheath 80 is moved to align the pins 92 on the sheath 80 with the first grooves 64 (FIGS. 4 and 7) on the inner side surfaces of the mounting ears 60. As the pins 92 move into the first grooves 64, the mounting ears 60 are spread apart because the distance between the bottom surfaces of the first grooves 64 is less than the distance between the pins 92. The beveled edges 92' on the pins 92 help facilitate the introduction of the pins 92 into the first grooves 64. As the pins 92 move into the first grooves and spread apart the mounting ears 60, the pins 92 pop into the through holes 62 in the mounting ears 60 so that the sheath is pivotally mounted on the collar 50. FIG. 18 illustrates the sheath 80 pivotally mounted on the collar 50.

Next, the sheath 80 is pivoted towards the protector 70 in the direction of the arrow in FIG. 17 until the sheath 80 contacts the outer surface of the protector 70 in the manner shown in FIG. 11. As can be seen from FIG. 11, with the sheath 80 positioned in contacting engagement with the outer surface of the protector 70, the outwardly angled or flared portions 88' of the side walls 88 of the sheath 80 partially embrace and overlap the protector 70. This allows the sheath 80 to be positioned closer to the central axis C so that the angle $\alpha$ is smaller than would otherwise be the case if the outwardly angled or flared portions 88' of the side walls 88 were not provided (i.e., if the side walls 88 of the sheath 80 were straight along their entire length). This can reduce packaging costs in that as the angle $\alpha$ increases, the completed assembly occupies more space. Thus by reducing the angle $\alpha$, the assembly can be packaged more compactly. The safety needle assembly shown in FIG. 11 represents the safety needle assembly in its final assembled state.

It is possible to vary the assembly steps described above. For example, existing equipment in facilities that manufacture needles may already have in place equipment which mounts a rigid sleeve on the hub to cover the cannula. To continue utilizing this equipment and avoid the need for completely redesigning the assembly equipment, the protector 70 can be mounted on the hub 20 before mounting the collar on the hub 20. Then, before mounting the collar 50 on the hub, the protector 70 is removed so that the collar 50 can be mounted on the hub 20. Thereafter, the protector 70 is once again mounted on the collar as described above to cover the cannula.

In another alternative, it may be possible to mount the protector 70 on the collar 50 before mounting the collar 50 on the hub 20. With this alternative, it would be necessary to ascertain the orientation or facing direction of the cannula bevel 42 through the plastic material forming the protector 70. Alternatively, this approach may be employed if the orientation of the sheath 80 relative to the bevel 42 on the cannula is not particularly significant.

As mentioned previously, the safety needle assembly shown in FIG. 11 can be packaged in the state shown in FIG. 11. In this case, the user would unpackage the safety needle assembly and attach it to a fluid handling device such as a syringe. Another alternative involves connecting the safety needle assembly shown in FIG. 11 to a fluid handling device such as a syringe as shown in FIG. 20, and then packaging the syringe and the attached safety needle assembly. With this latter alternative, additional concerns about packaging costs and efficiencies arise. Here, the packaging must be designed to enclose not only the safety needle assembly, but also the syringe 100. As viewed from the rear end, the finger flange 110 of the syringe and the sheath 80 represent the largest lateral dimensions of the syringe/safety needle assembly that must be enclosed in the packaging.

As shown in FIG. 19(a), if the sheath 80 is positioned so that it is located 90° rotationally offset from the finger flange 110 on the syringe, a relatively deeper package will be required to accommodate and enclose both the finger flange 110 of the syringe 100 and the sheath 80 of the safety needle assembly. This means that a greater amount of packaging material will be required to enclose both the finger flange 110 of the syringe and the sheath 80 of the safety needle assembly. In addition, the packaging of the syringe and safety needle assembly is typically performed by blister packaging in which plastic sheet material is drawn to form the package. Thus, to fabricate deeper blister packages, it is necessary to use thicker plastic sheet material so that the plastic material can be appropriately drawn to form the required package.

In contrast, by positioning the sheath 80 so that it is aligned with the finger flange 110 on the syringe as shown in FIG. 19(b), a shallower package can be used to accommodate and enclose both the finger flange 110 of the syringe and the sheath 80 of the safety needle assembly. Thus, a lesser amount of packaging material will be required to enclose both the finger flange 110 of the syringe and the sheath 80 of the safety needle assembly. Further, a thinner plastic sheet material can be used to form the package. Thus, significant advantages can be realized by appropriately positioning the sheath 80 relative to the finger flange 110 of the syringe.

FIG. 19(c) illustrates the maximum angular relationship between the sheath 80 and the finger flange 110 that does not affect the blister depth of the package. The syringe finger flange 110 has a smaller dimension Y and a larger dimension perpendicular to the smaller dimension. Generally speaking, the sheath 80 is oriented relative to the syringe finger flange 110 such that the outer edge of the sheath lies within the outer confines of the smaller dimension of the syringe finger flange.

As shown in FIG. 19(c), which is an illustration of the safety needle assembly mounted on a syringe as seen from the rear end (i.e., the plunger end of the syringe), orienting the sheath 80 relative to the syringe finger flange 110 so that the sheath (or the outer edge of the sheath 80 as seen from the rear) remains between the two planes P1, P2 helps ensure that the blister depth of the packaging is minimized to the extent possible. The planes P1, P2 are parallel planes which pass through the outer edge of the syringe finger flange 110 in the smaller dimension direction of the syringe finger flange and which are parallel to the central axis of the cannula (i.e., the central axis C in FIG. 1). As shown by the FIG. 19(a) illustration, when the sheath 80 is oriented relative to the syringe finger flange 110 so that the sheath (or outer edge of the sheath as seen from the rear) is outside the region between the two planes P1, P2, the depth of the blister packaging increases to a significant extent.

To properly position the sheath 80 relative to the finger flange 110 of the syringe, it is necessary to orient the sheath 80 at a known position relative to the hub flange 39. This can be accomplished using suitable equipment. In addition, it is necessary to appropriately configure the threads on the distal end of the syringe to ensure that when the hub 20 is connected to the syringe (i.e., when the hub flange 30 is screwed into the threaded end of the syringe), the sheath 80 is positioned at the desired rotational position relative to the finger flange 110 of the syringe based on the parameters described above.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A safety needle assembly comprising:
   a hub which includes a proximal end for connection to a syringe and a distal end;
   a cannula including a proximal end connected to the distal end of the hub, the cannula also including a lumen extending therethrough and a distal end;
   a collar formed separately from the hub and mounted on the hub, the collar being rotationally fixed on the hub and including a sheath mounting portion;
   a protector positioned over the cannula and covering the distal end of the cannula, the protector being removable to expose the cannula including the distal end;
   a sheath provided with an opening extending along at least a portion of a longitudinal extent of the sheath, the sheath being positioned outside the protector when the protector is positioned over the cannula, the sheath being pivotally connected to the sheath mounting portion of the collar to be pivoted, after removal of the protector to expose the cannula, towards the cannula so that the cannula passes through the opening in the sheath and is covered by the sheath.

2. The safety needle assembly according to claim 1, wherein the hub possesses an outer surface provided with at least one set of projections, the collar including an inner surface provided with a plurality of projections, the projections on the inner surface of the collar engaging the at least one set of projections on the outer surface of the hub to rotationally fix the collar on the hub.

3. The safety needle assembly according to claim 1, wherein the hub possesses an outer surface provided with two spaced apart sets of outwardly extending projections each extending over less than one-half of a circumferential extent of the outer surface of the hub, the collar including an inner surface provided with a plurality of inwardly extending projections, the inwardly extending projections engaging the outwardly extending projections in each set to rotationally fix the collar on the hub.

4. The safety needle assembly according to claim 3, wherein the outwardly extending projections in each set are in the form of teeth and the inwardly extending projections are in the from of teeth, the teeth on the collar extending around the entirety of an inner circumferential extent of the collar.

5. The safety needle assembly according to claim 2, wherein the hub includes an annular recessed region located distally of the projections on the hub, the collar including an inwardly directed annular ridge positioned distally of the projections on the collar, the inwardly directed annular ridge on the collar being positioned in the annular recessed region on the hub.

6. The safety needle assembly according to claim 5, wherein portions of the hub immediately adjoining the recessed region having an outer diameter that is greater than an inner diameter of the inwardly directed annular ridge on the collar.

7. The safety needle assembly according to claim 1, wherein the sheath mounting portion of the collar includes a pair of spaced apart mounting ears each provided with a through hole, the sheath including a pair of pins extending in opposite directions, each of the pins being fitted into the through hole in one of the upstanding mounting ears.

8. The safety needle assembly according to claim 1, wherein the distal end on the cannula is provided with a bevel that is rotationally oriented relative to the sheath such that when the bevel on the cannula is facing directly vertically upwardly as viewed from the distal end of the cannula, the sheath pivots in a vertical plane.

9. The safety needle assembly according to claim 1, wherein the distal end on the cannula is provided with a bevel that is rotationally oriented relative to the sheath such that when the bevel on the cannula is facing directly vertically upwardly as viewed from the distal end of the cannula, the sheath pivots in a horizontal plane.

10. The safety needle assembly according to claim 1, wherein the protector is at least mounted on a distal end portion of the collar.

11. The safety needle assembly according to claim 1, wherein the sheath includes a pair of opposite side walls and a back wall, the opening in the sheath being positioned opposite the back wall, the side walls including proximal portions that flare outwardly in a direction away from one another.

12. A safety needle assembly comprising:
  a hub which includes a proximal end for connection to a syringe and a distal end;
  a cannula including a proximal end fixed to the distal end of the hub, the cannula also including a lumen extending through the cannula and a distal end;
  a collar formed separately from the hub and mounted on the hub, the collar including a pair of spaced apart mounting ears;
  each of the mounting ears including two oppositely facing side surfaces, with one of the side surfaces of one mounting ear facing one of the side surfaces of the other mounting ear, each mounting ear having a width measured in a widthwise direction between distal and proximal ends of the mounting ear;
  one of the side surfaces of each mounting ear being provided with a first groove extending in the widthwise direction from a distal side of the mounting ear toward a proximal side of the mounting ear and the other side surface of each mounting ear being provided with a second groove extending in the widthwise direction from the proximal side of the mounting ear toward the distal side of the mounting ear, each of the mounting ears being provided with a through hole formed by the overlapping first and second grooves;
  a protector positioned over the cannula and covering the distal end of the cannula, the protector being removable to expose the distal end of the cannula;
  a sheath provided with an interior and an opening extending along at least a portion of a longitudinal extent of the sheath, the sheath including a pair of pins each positioned in the through hole in one of the mounting ears to pivotally connect the sheath to the collar at a position outside the protector to permit the sheath, after removal of the protector to expose the distal end of the cannula, to pivot towards the cannula so that the cannula passes through the opening in the sheath and is positioned in the interior of the sheath in a position covered by the sheath.

13. The safety needle assembly according to claim 12, wherein each of the mounting ears possesses a thickness measured between the side surfaces of the mounting ear, the first and second grooves in each respective mounting ear having a combined depth at least equal to the thickness of the respective mounting ear.

14. The safety needle assembly according to claim 12, wherein the collar is rotationally fixed on the hub.

15. The safety needle assembly according to claim 12, wherein the hub possesses an outer surface provided with two spaced apart sets of outwardly extending teeth, each set of teeth extending over less than one-half of a circumferential extent of the outer surface of the hub, the collar including an inner surface provided with inwardly extending teeth, the inwardly extending teeth on the collar engaging the outwardly extending teeth in each set to rotationally fix the collar on the hub.

16. The safety needle assembly according to claim 12, wherein the hub includes an annular recessed region, the collar including an inwardly directed annular ridge, the inwardly directed annular ridge on the collar being positioned in the annular recessed region on the hub.

17. The safety needle assembly according to claim 16, wherein portions of the hub immediately adjoining the recessed region having an outer diameter that is greater than an inner diameter of the inwardly directed annular ridge on the collar.

18. The safety needle assembly according to claim 12, wherein the protector is at least mounted on a distal end portion of the collar.

19. The safety needle assembly according to claim 12, wherein the sheath includes at least one locking element located within the interior of the sheath to engage the cannula and permanently lock the cannula within the interior of the sheath.

20. A method of assembling a safety needle assembly comprising;
  positioning a collar over the distal end of a hub in a way that permits relative rotation between the collar and the hub, the collar including a sheath mounting portion, and including a cannula having a proximal end fixed to the distal end of the hub, the cannula having a distal end provided with a bevel;
  identifying the bevel on the distal end of the cannula and effecting relative rotation between the collar and the hub to orient the bevel in a desired orientation relative to the collar;
  effecting axial movement between the hub and the collar while maintaining the desired orientation to locate the collar at a position relative to the hub at which the collar is rotationally fixed on the hub;
  positioning a removable protector over the cannula to cover the bevel on the distal end of the cannula, the protector being removable to expose the distal end of the cannula; and mounting a sheath provided with an interior and an opening extending along at least a portion of a longitudinal extent of the sheath at the sheath mounting portion of the collar to pivotally connect the sheath to the collar and permit the sheath, after removal of the protector, to pivot towards the cannula so that the cannula passes through the opening in the sheath and is positioned in the interior of the sheath in a position covered by the sheath.

21. The method according to claim 20, wherein the desired orientation of the bevel relative to the collar is an orientation in which with the cannula horizontally positioned and the bevel facing vertically upward, the sheath pivots in a horizontal plane.

22. The method according to claim 20, wherein the desired orientation of the bevel relative to the collar is an orientation in which with the cannula horizontally positioned and the bevel facing vertically upward, the sheath pivots in a vertical plane.

23. The method according to claim 20, wherein the collar hub includes a recessed region, the collar being positioned over the hub so that a ridge on the collar engages a step on the hub that adjoins the recessed region to prevent the ridge on the collar from being located in the recessed region.

24. The method according to claim 20, wherein the axial movement between the hub and the collar involves axially moving the collar relative to the hub, the collar being rotationally fixed relative to the hub by engaging inwardly directed projections on the collar with outwardly directed projections on the hub.

25. A safety needle assembly connected to a fluid transfer device comprising:

a hub which includes a proximal end and a distal end;

a cannula including a proximal end connected to the distal end of the hub, the cannula also including a lumen extending therethrough and a distal end;

a collar formed separately from the hub and mounted on the hub, the collar being rotationally fixed on the hub and including a sheath mounting portion;

a protector mounted on the collar and being positioned over the cannula to cover the distal end of the cannula, the protector being removable to expose the cannula including the distal end;

a sheath including an opening along one side, the sheath being positioned outside the protector when the protector is positioned over the cannula, the sheath being pivotally connected to the sheath mounting portion of the collar to be pivoted, after removal of the protector to expose the cannula, towards the cannula so that the cannula passes through the opening in the sheath and is covered by the sheath;

a syringe including a proximal end and a distal end provided with a hub mounting portion, a portion of the hub engaging the hub mounting portion so that the hub is connected to the syringe, the syringe having a finger flange shaped to possess a greatest dimension and a perpendicularly oriented smaller dimension; and the sheath being positioned relative to the finger flange such that when viewed from the proximal end of the syringe, an outer edge of the sheath lies within outer confines of the smaller dimension.

* * * * *